US006228372B1

(12) United States Patent
Reed et al.

(10) Patent No.: US 6,228,372 B1
(45) Date of Patent: *May 8, 2001

(54) **COMPOUNDS AND METHODS FOR THE DETECTION AND PREVENTION OF *T. CRUZI* INFECTION**

(75) Inventors: Steven G. Reed, Bellevue; Yasir A. W. Skeiky; Michael J. Lodes, both of Seattle; Raymond L. Houghton, Bothell; John M. Smith, Everett; Patricia D. McNeill, Des Moines, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/993,674

(22) Filed: Dec. 18, 1997

Related U.S. Application Data

(63) Continuation-in-part of application No. 08/834,306, filed on Apr. 15, 1997, now Pat. No. 6,054,135.

(51) Int. Cl.[7] ................................................. A61K 39/002

(52) U.S. Cl. ................................ 424/269.1; 424/185.1; 424/191.1; 424/192.1; 424/193.1; 424/200.1; 435/7.1; 435/7.22; 435/4; 435/7.4; 435/7.92; 435/69.1; 435/69.3; 435/69.7; 435/71.1; 530/300; 530/324; 530/333; 530/334; 530/344; 530/403; 530/412; 530/350

(58) Field of Search ........................... 530/350, 300, 530/324, 333, 334, 344, 403, 412; 424/269.1, 192.1, 185.1, 191.1, 193.1, 200.1; 435/7.4, 4, 7.1, 7.22, 7.92, 69.1, 69.3, 69.7, 71.1

(56) References Cited

U.S. PATENT DOCUMENTS

| 4,870,006 | 9/1989 | Dragon et al. ..................... 435/7.22 |
| 5,304,371 | 4/1994 | Reed ..................................... 424/88 |

FOREIGN PATENT DOCUMENTS

| 90/02564 | 3/1990 | (WO) . |
| 92/09895 | 6/1992 | (WO) . |
| 93/16199 | 8/1993 | (WO) . |
| 94/01776 | 1/1994 | (WO) . |
| 96/29605 | 9/1996 | (WO) . |
| 97/18475 | 5/1997 | (WO) . |
| WO 99/31246 | 6/1999 | (WO) . |

OTHER PUBLICATIONS

Bastos et al., "Use of recombinant peptide antigens of *Trypanosoma cruzi* in a diagnostic test for Charga's disease," *Memorias Do Instituto Oswaldo Cruz* 93(Suppl. II):286–287, Nov. 1998.

Campana et al., "Evaluation of specific synthetic peptide combinations in serodiagnosis of Chagas'disease," *Mem. Inst. Oswaldo Cruz.* 93(Suppl. II):234–235, Nov. 1998.

Houghton et al., Multiepitope synthetic peptide and recombinant protein for the detection of antibodies to *Trypanosoma cruzi* in patients with treated and untreated Changa's disease, *The Journal of Infectious Diseases* 181(1):325–330, Jan. 2000.

Buschiazzo et al., "Sequence of the gene for a *Trypanosoma cruzi* protein antigenic during the chronic phase of human Chagas disease," *Molecular and Biochemical Parasitology* 54: 125–128, 1992.

Campetella et al., "A Superfamily of *Trypanosoma cruzi* Surface Antigens," *Parasitology Today* 8:11, 378–381, 1992.

Frasch and Reyes, "Diagnosis of Chagas Disease Using Recombinant DNA Technology,"*Parasitology Today* 6:4, 137–139, 1990.

Frasch et al., "Comparison of Genes Encoding *Trypanosoma cruzi* Antigens," *Parasitology Today* 7:6, 148–151, 1991.

Hoft et al., "*Trypanosoma cruzi* Expresses Diverse Repetitive Protein Antigens," *Infect. And Immunity* 57:7, 1959–1967, 1989.

Ibanez et al., "Multiple *Trypanosoma cruzi* antigens containing tandemly repeated amino acid sequence motifs," *Molecular and Biochemical Parasitology* 30:27–34, 1988.

Peralta et al., "Serodiagnosis of Chagas' Disease by Enzyme Linked Immunosorbent Assay Using Two Synthetic Peptides as Antigens," *Journal of Clinical Microbiology* 32:4, 971–974, 1992.

Skeiky et al., "Antigens Shared by Leishmania Species and *Trypanosoma cruzi*: Immunological Comparison of the acidic Ribosomal P0 Proteins," *Infection and Immunity* 62(5): 1643–1651, 1994.

Skeiky et al., "Cloning and Expression of *Trypanosoma cruzi* Ribosomal Protein P0 and Epitope Analysis of Anti–P0 Autoantibodies in Chagas' Patients," *J. Exp. Med.* 176:201–211, 1992.

Skeiky et al., "*Trypanosoma cruzi* Acidic Ribosomal P Protein Gene Family," *Journal of Immunology* 151(10): 5504–5515, 1993.

Vergara et al., "Assay for Detection of *Trypanosoma cruzi* Antibodies in Human Sera Based on Reaction with Synthetic Peptides," *Journal of Clinical Microbiology* 29:9, 2034–2037, 1991.

*Primary Examiner*—Jennifer Graser
(74) *Attorney, Agent, or Firm*—Seed Intellectual Property Law Group

(57) ABSTRACT

Compounds and methods are provided for diagnosing *Trypanosoma cruzi* infection. The disclosed compounds are polypeptides, or antibodies thereto, that contain one or more epitopes of *T. cruzi* antigens. The compounds are useful in a variety of immunoassays for detecting *T. cruzi* infection. The polypeptide compounds are further useful in vaccines and pharmaceutical compositions for inducing protective immunity against Chagas' disease in individuals exposed to *T. cruzi*.

13 Claims, 10 Drawing Sheets

SEQUENCE LISTING (1) GENERAL INFORMATION:

(iii) NUMBER OF SEQUENCES: 81

(2) INFORMATION FOR SEQ ID NO:1:

(i) SEQUENCE CHARACTERISTICS:
    (A) LENGTH: 518 base pairs
    (B) TYPE: nucleic acid
    (C) STRANDEDNESS: single
    (D) TOPOLOGY: linear (xi) SEQUENCE DESCRIPTION: SEQ ID NO:1:

```
CGGGAAAAGA AGGCTGTTAC GACGCACGAG CTTGGCTTTG AGGGCGAGGA CTGGGACTAC      60

GTGCTGGAGC GGCGGCGCGC GGAGGTGAAG GACGTGCTGG CCGTCGAGAC GGCGCGGGCG     120

TTGGGACTCG AGCGTGAGGA CGTGCTGGAG GTGGAGGTCG ACGCAGTGCC TCGGAGCCTC     180

ATTGCGTTTG TCACGGTCCG TCATCCATCA CTGCTGAGCG ACCGCAGGTG GAAGAGACGC     240

TGGCGCGCTG CGAGTACAGG AAATTGTGGG CGCTGTACGA GACGCGGCCA CTGGAGTCGT     300

CAGTGCTGAT GAGGCGGTTT GAGGGCGACG ACTGGGACCT CGTGGTTGAC AACAACCGCA     360

GGAAGCTTGA GGACGCGTTC AGCAGGGAGA CGGCCGCGCA CTGGGCGTGT CGCCGAGGCA     420

GGTTGTGCTT CTGGACTGCA GGGTTGGCAG CCTTCTCATG GTATTCAAGG TGCTTGGATG     480

CGCCATGAGC GACGCAGAGA TCACGGAACG GACCGAGG                             518
```

(2) INFORMATION FOR SEQ ID NO:2:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (xi) SEQUENCE DESCRIPTION: SEQ ID NO:2:

```
CGGCGGTAGT CTGCGATGCT GTGGACCGAC GCATTGAAAT ACACACCGTC TTCGGCGTTC      60

CTTTTTTTTA TATGTTTTTT TTTATTGAGA AGATGTCTTG TTTGTTGTTG TTTTTTTTCA     120

GTTTTTATGA TACGAGCAGT TTGTCCGACT GCATTCATGC AGTGATTGGT AATTCTTTCT     180

ATTCTTTGGA ATTATGGCGA TATTATTCTT GTCTTTTAAA ATTCTTACAA CCAATTGTGC     240

CTTAGAGTTT CCTGCTTAGT TGCTATTAAC ACACTGTTAG GAACGCGAAA CCATGCAGAT     300

CTTCGTGAAG ACACTGACGG GCAAGACGAT CGCGCTCGAG GTGGAGTCCA GCGACACCAT     360

TGAGAACGTG AAGGCGAAGA TCCAGGACAA GGAGGGTATC CGCCGGACCA GCAGCGCCTG     420

ATCTTCGCTG GCAAGCAGCT GGAGGACGGC CGCACGCTCG CAGACTACAA CATCCAGAAG     480

GAGTCCACGC TGCACCTTGT GCTGCGCCTG CGCGGCGGCA TGCAGATCTT CGTGAAGACA     540

CTGACGGGTA AAGACGATCG                                                 560
```

(2) INFORMATION FOR SEQ ID NO:3:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (xi) SEQUENCE DESCRIPTION: SEQ ID NO:3:

```
CGGCTGCCTC CTCTGCTTCC TTCCTCGGAC GTGCCCGAAG GCATGGAGCT GCCTCCTCTG      60

CTTCCTTCCT CGGACATACC CGAAGGCATG GAGCTGCCAC CTCTGCTTCC TTCCTCGGAC     120

GTACCCGCGG GCATGGAGCT GACACCTCTG CTTCCTTCCT CGGACGTGCC CGAAGGCATG     180

GAGCTGCCAC CTCTGCTTCC TTCCTCGGAC GTACCCGCGG GCATGGAGCT GCCACCTCTG     240

STTCCTTCCT CGGACGTACC CGCGGGCATG GAGCTGCCTC CTCTGCTTCC TTCCTCGGAC     300

GTACCCGCGG RCATAGAGCT GCCACCTCTG ATTTCCTNCC TCGGACGTAC CCNCAGGNAT     360
```

```
GGAGATGNCT CCTCTGNTTC CTGCCTCGGA CGTNCCCNAA GGNATAGAGN TGCNCCTCTG       420

NTTCCTNCCT CGGAAG                                                      436
```

(2) INFORMATION FOR SEQ ID NO:4:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO:4:

```
CCTCAGGGGC TCTTGGCGTT CCTTTTTTTC TTGTTGTTTT GAGTTTTTTT TTCTTTTGTT        60

TTGGTTTGTC GTCTCTGTTT TTATGTGCGT TGTTTTCGGT TTTTCTTTTT GTTCTTCCTG       120

CCTGTCATGT GACTAGTTTT ATGTTTTCCA GGCCGACCGT CACTCAATTT TTTTATTTTT       180

ATTTTTATTT ATTTATTTGA CCCGCCTTTC TCTGTAGTTT ACGAGAGTTT AGATTTTTAT       240

TGATTGGTAG TTTAGGGCCA TCAGGCGGGA GGGGCGAGTC TGGCGGAAGA CAAAACAAAA       300

TACGATGGAC TCGACCAACA GCATCGAGAA ATCGCTTCTG ATGGAGATGG AGCGGGAGGT       360

TGAGAGGGCG AGG                                                         373
```

(2) INFORMATION FOR SEQ ID NO:5:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (xi) SEQUENCE DESCRIPTION: SEQ ID NO:5:

```
CAGAAAAAGA ACGTAGATTT CCAACCAAAA CAGCAAGAGC GGATCCAACA ACGACCAAAC        60

AACTCATTAT TCGAGCTCTC CAAAATATAT CGCTTGCCTT CGGGATTGAA CCCTCATCTA       120

CAGTAAAATA CGCCGAAAGC ACGCAAGAAG AAAATGGAAA ACGTTCACAA AGTGAGGCCG       180

AGGAGCGTGC ACGGCGGGAG GCTGAGGAAC GAGCACGGCG AGAGGCTGAG GAACGAGCCC       240

AACGAGAGGC TGAGGAACGA GCCCAACGAG AGGCTGAGGA ACGAGCACGG CGGGAGGCTG       300

AGAAGCGTGC CCGGCGAGAG GCTAAGGAAC GAGCATGGCA AGAGGCCGAA GAACGAGCCC       360

AACGAGAGGC TGAGGAGCGT GCCCGGCGAG AGGCTGAGGA GCGTGCCCGG CGAGAGGTTG       420

AGGAGCGTGC CCGGCAAGAG GCTGAGGAAC TCGCACGGCA AGAGTCTGAG GAACGTGCAC       480

GGCAAGAGGC CGAAGAACGA GCATGGCAAG AGGCTGAGGA GCGTGCCCAA CGAGAGGCTG       540

AGGAGCGTGC TCAACGAGCG                                                  560
```

(2) INFORMATION FOR SEQ ID NO:6:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (xi) SEQUENCE DESCRIPTION: SEQ ID NO:6:

```
GCCTCCTGCA ACTCGAGCTG GCAGCGTGGA GGTGCNGCAG GAACTCTCAA NAGANGACGG        60

CTCTCCCTCG ATANCNTTCG GAGTGACTTN GACTGTTGCG CCNTTTCCGT NTCACTATTT       120

CTATTGCTTT TAATTTGCTG GAGAGGCGCG TGTAGGAGGG AAAGAGTAGT AACATGGCAG       180

AATCATCAAA AACGATGTTG CGTTAGTAGA GAGGAGGGAA ACATCGAGAC GTTGAGGGTT       240
```

```
GCGACGGNCA AAATTATGTA CATTTACCTG AATTAGGATA AGACTTCATA TGGCATAAAC      300

TCGTGGCGTT GTTGGTGGTT ATAACAAGCA ACGGTGACGA TGTCTTAGGC TACACTGCTG      360

CACTCAAAGA GTTTTACAGG TACTTGCGGG ATATTTGTTC CTGTGAGTTT GTTTTCTATT      420

GTAATTTATT NNGTCTCAAT                                                  440
```

(2) INFORMATION FOR SEQ ID NO:7:

(i) SEQUENCE CHARACTERISTICS:
        (A) LENGTH: 1915 base pairs
        (B) TYPE: nucleic acid
        (C) STRANDEDNESS: single
        (D) TOPOLOGY: linear (xi) SEQUENCE DESCRIPTION: SEQ ID NO:7:

```
CGATGCGTCT GTCGTAGACC TGGGAGGCGA GGCCCATGGG ACACACTATG CCTTTTTGCC       60

CGATGTGATC AAGGGGATTG CGCAGGAAGA GCTGTACCTG GAAGACGATG CGTACTTCCA      120

GGAGTTGCTT GCGAGGTATA AGAACTTGT  CCCTGTGGGT GCCGAGCCAA CCGAGCCACG      180

CGCAAAGCAG TTGCGCGAGC AAATGCGGAT ACGGGCTGGG CAGCTTGCTG TTGACACCCG      240

AAAGCTTCAT GCGGCCGAAG AGCGGGCTGC ATCGCGGATG GCGACACTTT ACCCGTTTGT      300

GGGCTCGGCG CCGCTGGGAG TTGCTCTGTG GAATATCCCC GTGGAGGCGG ACGAAGAGTT      360

CTGTGCACTT CTGCTGAAGC GCGAAGAAGC GCTGGCGGGG AAGTCAGGGT CCGTCCACGA      420

AGTGGAATCT GCGCTGAGCG CGCGTGCGGA AGCGATGGCG AAGGCGGTGC TGGAGGAGGA      480

GGAGGCGCTT GCGGCGGCAT TTCCATTTCT GGGGCGGAGT GTTAAGGGAG CCCCTCTGCG      540

TGAGTTGGCT CTCATGTCTG ATCCCAATTT TGCGGAGCTG GCGACACGGC ACGCGCAGGA      600

GGCGACCTCG GGCGATGCGG CGGGTATTTT GCGCCTTGAG CAGGAGCTGC GTGACCAGGC      660

ATGTCGCATA GCACGTGAGG TGCGAGTGGC TCGGCGGCTT GACGCCGTCG CAATGAGGAC      720

CTGCACGAGC GGTACCCGTT TCTTCCCGAG GAGCCGGTGC GCGGCATTCT TCTTGGTGCT      780

GTGCGTCCGG TGCAGCAACC GGCGTTCCGC GAGCTTTCAA ACAAGTTGGA TGAGCAGCGC      840

CGGGACCCGA CACGCAACGC AGCCGCGATC CGCACGACGG AGGAGCAGAT GACTGCGTTG      900

GTGGTGCGAC TGGCTGAGGA GCGCGCGGAG GCGACGGAGA GGGCGCATGA GCAGTACCCG      960

TTTCTCCCAC GACGTGTGCT GGGCGTGCGC CTTGGTGACA TCTCGCTGCA GGAGGATGAT     1020

GTGTTGTCAC AGCTGGCGCG GCGTCGTGTG CGGCAGCTAA GAAACTCCAA GACGGCGATT     1080

GACGCACACG CAACTGAAGA AGAGATGATA AGGCGCGCAG AGGAGCTGGC TCGCAACGTG     1140

AAGCTTGTCG ACGCATACCG TGGGAATGGG AACGAGTACG TGCGTGCCTG CAACCCGTTT     1200

CTCGTGTACG AGGACCGCAA GTGCGTCCTC CTGAGTGAGC TGCCGCTTGC CGGTGGCGAC     1260

GTGTACCAGG GCTTGTTCCG GGATTATCTG ACTGCGCTGG AGGACGCCGA GGCAAATGCA     1320

CCGCGGATCG CGGAGCTGGA GAATGCGCTT CGGTCCCGTG CGGATGAGTT GGCGCTGGAG     1380

GTTTGCGAGA GGGACGCGCG GTTGTTGCAT TACTCATTCC TCTCGGCCCA GGATGTTCCT     1440

GGTTGGTCTG AAGCACTGCT GCATGACGCG GAGTTTCAGC AGCTACGTGA GCGTTACGAG     1500

GAACTGAGCA AGGATCCACA GGGGAACGCC GAGGCATTGC GTGAGCTTGA GGATGCAATG     1560

GAGGCTCGGA GCAGAGCCAT TGCGGAAGCG TTGCGGACTG CAGAGCGACT AATCCACTGA     1620

GCAGGCGAGG CTGAAGACGC CGTCACAGGC GGGGTCTGGC GTGTCCGCGG GTGATCGAAT     1680

GCATGGCAGC GAGCATGCGG ATCTCGCGCA TGAAGGGGGA AGCACGGCTG GCGGCACCAT     1740

GAGGGGGGCA GAGTCTGTCT CCAAGAGCAG TGGGAAACAC TCTCAAGGTC GGTCTCGCAT     1800
```

```
GCGTCTGTCG TAGACCTGGG AGGCGAGGCC CATGGGACAC ACTATGCCTT TTTGCCCGAT    1860

GTGATCAAGG GGATTGCGCA GGAAGAGCTG TACCTGGAAG ACGATGCGTA CTTCG         1915
```

(2) INFORMATION FOR SEQ ID NO:8:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (xi) SEQUENCE DESCRIPTION: SEQ ID NO:8:

```
TTACCAAGCT GAGATAGATA AAAGGCTGCA GGAGCAGCTT GCCCCTGAGA GGATGAGGGC      60

TCTTTCCGCA TTTCTTTCGG AGTGACTTTG ACTGTTGCGC CGTTTCCGTG TCACTATTTC     120

TATTGCTTTT AATTTGCTGG AGAGGCGCGT GTAGGAGGGA AAGAGTAGTA ACATGGCAGA     180

ATCATCAAAA ACGATGTTGC GTTAGTAGAG AGGAGGGAAA CATCGAGACG TTGAGGGTTG     240

CGACGGNCAA AATTATGTAC ATTTACCTGA ATTAGGATAA GACTTCATAT GGCATAAACT     300

CGTGGCGTTG TTGGTGGTTA TAACAAGCAA CGGTGACGAT GTCTTAGGCT ACACTGCTGC     360

ACTCAAAGAG TTTTACAGGT ACTTGCGGAT ATTTGTTCCT                           400
```

(2) INFORMATION FOR SEQ ID NO:9:

(i) SEQUENCE CHARACTERISTICS:
        (A) LENGTH: 936 base pairs
        (B) TYPE: nucleic acid
        (C) STRANDEDNESS: single
        (D) TOPOLOGY: linear (xi) SEQUENCE DESCRIPTION: SEQ ID NO:9:

```
GCCTCCTGCA ACTCGTGCTG GCAGCGTTGA AGTTCGGCAG AAATCTCAAC AAACGCCTTC      60

TGTCCCTCGG AAACCTTCCC GTTAAGAGAC ACAAGCAGTT CAATGAGCGA CATGGTCGCT     120

TCGGACACGT CCAATGCTTT CATGGTTTGT TCCAGCCGCC GCTGAAAGTT ATCCACACAT     180

GAGAACAACA AAGACAAATC TAAATCGGCG TCGCCGTGCT CATACACATC AAACGCCACC     240

GTCTCGCCCA AACATTCAA AAAGTTCACC AAAAAGTTTA CAAGCTTACT CAAATTGTCA     300

CGAAGTGAGC TAACGGTAAT TTCTAAACTT CCATTTCTTG CGTCATCCCT AGCCTTCGCC     360

GCGACTACCT TCTCCTTCCA TAGCACTAGC TTCTCCTCCA CCAAACGAAT ACCGCTCTCC     420

TTTTCTTTCA CAGCAACCTC ACATTCCCTT TCAATTTCAT TCAACCTAAT TGGATTATTT     480

TCTTAAACGA CTTGCCGTGC CCTCCTGGG CTGATGAAAG GCCTCGCCCA GCTGCGCACG     540

CAGATTCACG GTGTCCGCCC CGTTCTGCTC CCGGAGAGCG GCCAGTTCCT CGGTGGTTCG     600

CTTCAGCTCG CGATGCACCT CCTCGCGCTG CTGCAAGGCC TCGTCCAGCT GCGCACGCAG     660

ATTCACGGTG TCCGCCCCGC TCTGCTCCCG GAGAGCGGGC AGTTCCTCGG TGGTTCGCTT     720

CAGCTCGCGA TGCACCTCCT CGCGCTGCTG CAAGGCCTCG TCCAGCTGCG CACGCAGATT     780

CACGGTGTCC GCCCCGCTCT GCTCCCGGAG AGCGGGCAGT TCCTCGGTGG TTCGCTTCAG     840

CTCGCGACGC ACCTCCTCGC GCTGCTGGAA GGCCTCGCCC AGCTGCGCAC GCAGATTCAC     900

GGTGTCCGCC CCTCTCTGCT CCCGGAGGGC GGGCAG                               936
```

(2) INFORMATION FOR SEQ ID NO:10:

(i) SEQUENCE CHARACTERISTICS:
        (A) LENGTH: 702 base pairs
        (B) TYPE: nucleic acid (C) STRANDEDNESS: single
                (D) TOPOLOGY: linear (xi) SEQUENCE DESCRIPTION: SEQ ID NO:10:

```
ACTTGAAAGA NTGACCCAAT AATNGGGTTC CTTATTGTGC CACCCCAAAT AAACCCGTAA      60

CCAATTTGTG GCTGGGATGG ATCCCCCCAC NCTCTTTGAC NCATGTCAAG AGTANATGGG     120

ACGTCAAAGT CACTTAGAGA GGGATTCATG GGTNCCATTG ATCACAAGAG CCTNCTGGAA     180

GACCCCCGTG AAGATAACCC AATGAGATTT ATCGTCTGCA TAAGATCACA CGAGGCGGTA     240

TTAGCAATTA TCTTCACAGA TTCTTTTTCT TGTGATGGTG GCTTGCGGTA GTTTGTCATC     300

ATTGTTTTCT GAATGCAATG AAGCACACGA CTTGTAATAC GTTCTCCATG TCTTTCAATC     360

GTTTCCAACG CCTCCACAAT GTCTGCAGGA TCCCCAGGAA GGTCAGCAGT CATCAGAAGC     420

TCTTCACATG AACGCCGTAA ACTAGGATCA CGCTCAACAA GGCTAGCAAT CGCATTTGCC     480

ATTCTCGGAT TCCACTTGCA AAACCACTCC GGAAGTTTAT TTCCACGACT GACCTCTGTC     540

ATAATGTTGA ACCTCTCCCT AAAGCCTTTA CCCGCCACGG CAAGCCACAT CTCAAGAGCT     600

ATCATACCCA GGCTGTATTC ATCCACTTTA AAGTCGTAGT CTTCCCCTCG CTCTTGCTCT     660

GGGGCACAGT ACAACACAGA ACCCAAGTTT CCTGTAGGAC CG                       702
```

(2) INFORMATION FOR SEQ ID NO:11:

(i) SEQUENCE CHARACTERISTICS:
            (A) LENGTH: 510 base pairs
            (B) TYPE: nucleic acid
            (C) STRANDEDNESS: single
            (D) TOPOLOGY: linear (xi) SEQUENCE DESCRIPTION: SEQ ID NO:11:

```
CGAGTATTCC TGTGGAAATT GATATTAGAA ACCAGGACTT TTCTTTTCTT GACCCGGCAC      60

CGGAGGGCAT TCCTATTCAG GACATACATC TTATGGGAGA TTCTGCATTT GCCGCATCTG     120

CGCGTGAGCG CATGAAACTG AAAAGAAATC CTGTTGCGAA TGCGAGCAAG ATCAGTGCCC     180

TTGAGGAGGA GATGGATCAA CGTGCTCATG TATTGGCTAA GCAGGTGCGT GACAAAGAGC     240

GCACTTTCCT TGATCCAGAG CCTGAGGGTG TTCCACTTGA GTTGCTTTCA TTAAATGAAA     300

ATGAGGCCTC ACAGGAATTG GAGCGAGAGC TTCGTGCCCT AAATCGCAAA CCCCGGAAGG     360

ATGCCAAAGC AATAGTTGCT CTTGAAGATG ATGTGCGTGA CGAACACACG TGCTTGCCAA     420

GGAGCTAAAG GAAAATGAGC GGAACATCTT TGTTGGCTCC ACAGCCTGAG GGTGTGCCGG     480

TGTCTGAGCT GTCGTTGGAT TTAGACGAGC                                     510
```

(2) INFORMATION FOR SEQ ID NO:12:

(i) SEQUENCE CHARACTERISTICS:
            (A) LENGTH: 320 base pairs
            (B) TYPE: nucleic acid
            (C) STRANDEDNESS: single
            (D) TOPOLOGY: linear (xi) SEQUENCE DESCRIPTION: SEQ ID NO:12:

```
CGGTCGTGGC AGAGCCAAAG CCACCAACAG CAGGTGCCGA CGTGTGCGCG GCAGAGCCGA      60

AGCCACCAGC AGCAGGCGCC GAAGTGGTCG TGGCAGAGCC AAAGCCACCA GCAGCAGGTG     120

CCGACGTGTG CGCGGCAGAG TCGAAGCCAC CAACAGCAGG TGCCGACGTG GTCGTGGCAG     180

AGCCAAAGTC ACCAGTAGTA GGNGCCGACG TGTGNGTGGC AGAGNCANAG NCACCAGTAG     240

NAGGTGNCGA CGTNGTCGTG GNAGAGNCGA NGTCACCAGC AGGAGGTGNC GACGTNTGNG     300
```

NGGNAGAGGC GATGTCACCA                                        320

(2) INFORMATION FOR SEQ ID NO:13:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (xi) SEQUENCE DESCRIPTION: SEQ ID NO:13:

ATGCATCTCC CCCGTACATT ATTTTGCGGA AAATTGGATT TTTACGGGGA GGTGGGGTTC    60

GATTGGGGTT GGTGTAATAT AGGTGGAGAT GGAGTGCAGT GGGATAGGAT TAGAATGTAG   120

TTGGTGTAGT ACAGAGTTTA TATAGTATAG TGTTGATGTT ATTATACAAT GAGGTAAGAG   180

AATGGAGTGA GAAAGAGTAT GTTTGTTAGT TTGGTTGTTA ATGTTATGTA TTCATGTTAT   240

CAGTATATGT TGTATGTGTA TGGTGATAGC GGTGGGTGTA GCTGTATGTG GTAGGTTAGA   300

GT                                                                 302

(2) INFORMATION FOR SEQ ID NO:14:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (xi) SEQUENCE DESCRIPTION: SEQ ID NO:14:

CAGTTTCAAT TTCCTCTCCA CCTGATCCCG CTGTTGCAAA AGCGTCCTTG ATGTATCCTG    60

CTCCTTTGCC GCTAGCGCCT CCCTTGCTAA GCGCAGTTCC TCTTGCAGCC TCGCCTGCAC   120

CCGTTCCGCC TCCATTAATC TCTTCTCCCC GATTGCTTCT TTGGCGCGTA AATCCTCCAG   180

TTCCTTCTCT ATCAAAGTGT GCCTCCCATT CCTGATCCGC GACTCTTCAC AGGCTTCTTG   240

CTCCGCGTCA CGGAGACGCC TCTTGAGAGC CTCGTTCTTC TCTTCCAGGT CTTCTGGG    298

(2) INFORMATION FOR SEQ ID NO:15:

(i) SEQUENCE CHARACTERISTICS:
        (A) LENGTH: 2144 base pairs
        (B) TYPE: nucleic acid
        (C) STRANDEDNESS: single
        (D) TOPOLOGY: linear (xi) SEQUENCE DESCRIPTION: SEQ ID NO:15:

CGCGGAATTC TTACCAAGCT GAGATAGATA AAAGGCTGCA GGAGCAGCTT GCCCCTGAGA    60

GGATGAAGGC TCTTTCCACA TTTCTTTGGG AGTGACCTTG ACTGTTGCGC CGTTTCCGTG   120

TCACTATTTC TATTGCTTTT AAATTGCTGG AGAGGCGCGT GTAGGAGAGA AAGAGTAGTA   180

ACATGGCGGA ATCATCAAAA ACGATGTTGC GTAAGTAGAG AGGAGGGAAA CATCGAGACG   240

TTGAGGGTTG CGACGGCCAA GATTATGTAC ATTTACCTGA ATTAGGATAA GACTTCATAT   300

GGTATAAAGT CGTGGCGTTG TTGGTGGTTA TAACAAGCAA CGGTGACGAT GTCTCAGTCT   360

ACACTGCTAC AATCAAAGAG TTTTACAGGT ACTTGTGGAT ATTTGTTCCT GTGAGTTTGT   420

TTTCTATTAT AATTTATTTT GTCTCAATTT TTTGTTTCCC CGCTTCCTAC GGTCTCTTTT   480

TTTCTTCGTT CTTGAAATTT CAATTATTGC TTAACCACAA GCATCCAGTA CTTCAACCTC   540

CCCATCAAAT GGTGTCGCTG AAGCTGCAGG CTCGTTTGGC GGCGGACATT CTCCGCTGCG   600

GTCGCCACCG TGTGTGGCTG GACCCTAATG AGGCCTCTGA GATTTCCAAT GCAAACTCGC   660

-continued

```
GCAAGAGCGT GCGCAAGTTG ATCAAGGATG GTCTGATTAT TCGCAAGCCT GTCAAGGTGC      720

ACTCGCGCTC CCGCTGGCGC CACATGAAGG AGGCGAAGAG CATGGGCCGC CACGAGGGCG      780

CTGGGCGCCG CGAGGGTACC CGCGAAGCCC GCATGCCGAG CAAGGAGCTG TGGATGCGCC      840

GTCTGCGCAT TCTCCGCCGC CTGCTGCGCA AGTACCGCGA GGAGAAGAAG ATTGACCGCC      900

ACATTTACCG CGAGCTGTAC GTGAAGGCGA AGGGGAACGT GTTTCGCAAC AAGCGTAACC      960

TCATGGAGCA CATCCACAAG GTGAAGAACG AGAAGAAGAA GGAAAGGCAG CTGGCTGAGC      1020

AGCTCGCGGC GAAGCGCCTG AAGGATGAGC AGCACCGTCA CAAGGCCCGC AAGCAGGAGC      1080

TGCGTAAGCG CGAGAAGGAC CGCGAGCGTG CGCGTCGCGA AGATGCTGCC GCTGCCGCCG      1140

CCGCGAAGCA GAAAGCTGCT GCGAAGAAGG CCGCTGCTCC CTCTGGCAAG AAGTCCGCGA      1200

AGGCTGCTGC ACCCGCGAAG GCTGCTGCTG CACCCGCGAA GGCCGCTGCT CCACCCGCGA      1260

AGACCGCTGC TGCACCCGCG AAGGCTGCTG CACCTGCCAA GGCTGCTGCT CCACCCGCGA      1320

AGGCTGCTGC TCCACCCGCG AAGACCGCTG CTCCACCCGC GAAGACCGCT GCTCCACCCG      1380

CGAAGGCTGC TGCTCCACCC GCGAAGGCCG CTGCTCCACC CGCGAAGGCC GCTGCTCCAC      1440

CCGCGAAGGC CGCTGCTGCA CCCGCGAAGG CCGCTGCTGC ACCCGCGAAG GCTGCTGCTC      1500

CACCCGCGAA GGCCGCTGCT CCACCCGCGA AGGCTGCTGC TCCACCCGCG AAGGCTGCTG      1560

CTCCACCCGC GAAGGCTGCT GCTGCTCCCG TTGGAAAGAA GGCTGGTGGC AAGAAGTGAA      1620

GCGCGCACTA GTACGACCAA CTTGTTTTTT TTTTTGGTAT TTAATATTTT CTGAGGAAGA      1680

AGTGGGTATT GAGGGTCTTT CTTTCCGCGT TTGTGTTGGT TTGTGGTGTT CGTGACATTA      1740

TAGTAGATCC AAAGTATTCT TCAGTGTCCC TTTTCCTTTT CTCCATCCTT TTTCCTATTT      1800

TTTGTTTGTC TTCTCTACGA TCTTTGTTGT CGTGTGACCT CCGCTGTATG GAACTGACGG      1860

CCGGCGTTGT GAGAGACGAT GTCGCACGTC ACGGCGGACC TGGAGTATTT TAAATGTGAC      1920

ATGTGCGGGG TGTATCTGCA CAAAGACATC TTTTGCGACC ATCGACGTGA GTGTAAAGGC      1980

CTTGATTCGA AAGAGCTGAA GAAGAGCCAG TGTCGTCAGA TCGGGATGGC ATTAGACAAG      2040

GAGGCACGGC ACCGAATTGC GTCACGAATG GCTGATGGAG CAACTCTCGT GCCTGTCGAG      2100

CTTGCAGAAC GACATCAACA GGCGCGTGTG CGGCGTAATG TGGC                      2144
```

(2) INFORMATION FOR SEQ ID NO:16:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (xi) SEQUENCE DESCRIPTION: SEQ ID NO:16:

```
TGTGCTGCAG AAGGAGAGGG ATGAAGCCGT GGCGGAGAAT GCCCAGCTGC AGAAGGAGAG      60

GGATGACGCC GTGGCGGAGA ATGCCCAGCT GCAGAAGGAG AGGGATGACG CCGTGGCGGA      120

GAATGCCCAG CTGCAGAAGG AGAGGGATGA CGCCGTGGCG GAGAATGCCC AGCTGCAGAA      180

GGAGAGGGAT GACGCCGTGG CGGAGAATGC CCAGCTGCAG AAGGAGAGGG ACGAAGCCGT      240

GGCGGAGAAT GCCCAGCTGC AGAGGGAGAG GGATGACGCC GTGGCGGAGG ATGCCCAGCT      300

GCAGAAGGAG AGGGATGAAG CCGTGGCGGA GAATGCCCAG CTGCAGAGGG AGAGGGATGA      360

AGCCGTGGCG GAGAATGCCC AGCTGCAGAA GGAGAGGGAT GACGTCGTGG CGGAGAATGC      420

CCAGCTGCAG AAGGAGAGGG ATGACGCCGT GGCGGA                               456
```

(2) INFORMATION FOR SEQ ID NO:17:

(i) SEQUENCE CHARACTERISTICS:
    (A) LENGTH: 2446 base pairs
    (B) TYPE: nucleic acid
    (C) STRANDEDNESS: single
    (D) TOPOLOGY: linear (xi) SEQUENCE DESCRIPTION: SEQ ID NO:17:

```
TGAAGGCCGT TGATCCTTTT CAGGGAACGA CACCGCCGCC CTATAAATGG CAAGAAATGA      60

CTGGATCTGA GGCGGCAGCC GGCTCGCTTT GTGTACCCAG CCTTGCTGAG GTGGCCGGCG     120

GTGTGTTTGC CGTTGCTGAA GCTCAGCGCA GTGAAAGGGA CGAAGCCTGC GGCCATGCTG     180

CGATTGCAAC AACGCACATT GAGACGGGCG GTGGTGGCTC AAAGGCGATC TCGGCGATGG     240

ATGCAGGCGT TTTTCTCGTA GAACTTGTGG ATGCCGCCAG TGGTACGATC AGGACACGAG     300

AAAAGATGCA GCCAACGACA ATTGTGAGCG GCGACACTAT CTACATGGCC CTTGGGGACT     360

ACGAGAAGAA GACGTCTGGG GGTCGGGCTG CCGATGCAGA TGGCTGGAGG CTTTTACTGA     420

TGAGGGGAAC TCTCACTGAG GATGGTGGGC AGAAGAAAAT CATGTGGGGT GATATCCGTG     480

CAGTGGACCC TGTGGCCATC GGGCTTACTC AATTCCTGAA GAGGGTGATC GGTGGCGGAG     540

GATCGGGTGT TGTGACGAAG AACGGTTACC TTGTGCTTCC CATGCAGGCA GTAGAAAAGG     600

ATGGAAGGAG TGTTGTACTG TCCATGCGTT TCAACATGCG TATAGAAGCA TGCGAGCTCT     660

CGTCCGGTAC GACAGGTAGT AACTGCAAGG AACCATCCAT CGCGAATTTG GAAGGAAATC     720

TAATTTTAAT TACTTCTTGC GCTGCCGGCT ACTACGAAGT ATTCAGGTCC CTTGACTCTG     780

GGACAAGTTG GGAAATGAGT GGTAGGCCAA TTAGTCGCGT GTGGGCAAC TCGTATGGTC      840

GAAAAGGGTA TGGCGTTCGC TGTGGCCTCA CCACCGTAAC CATTGAGGGA AGGGAAGTGC     900

TGCTTGTTAC CACGCCAGTG TATTTGGAGG AGAAAAATGG TAGGGGTCGG CTTCATCTTT     960

GGGTGACGGA CGGTGCACGT GTGCATGATG CTGGGCCGAT ATCCGATGCA GCTGATGACG    1020

CTGCTGCCAG TTCCCTGTTG TATAGCAGTG GGGCAATCT GATTTCGCTG TACGAGAATA     1080

AGAGTGAGGG GTCATACGGT CTTGTTGCTG TGCACGTGAC TACGCAGCTG GAGCGGATAA    1140

AGACTGTGTT GAAGAGGTGG CAGGAGTTGG ATGAAGCCCT AAGAACGTGC AGATCCACTG    1200

CCACTATCGA CCCGGTGAGA AGGGGCATGT GTATTCGTCC CATTCTTACT GACGGGCTTG    1260

TTGGCTATTT GTCTGGTCTG TCGACTGGGA GTGAGTGGAT GGACGAGTAC CTCTGCGTGA    1320

ACGCAACTGT TCATGGGACG GTGAGAGGGT TCTCCAATGG AGTGACGTTT GAAGGACCCG    1380

GAGCAGGGGC GGGGTGGCCT GTTGCCCGAA GTGGACAGAA TCAACCGTAC CATTTCTTAC    1440

ACAAAACGTT CACTCTAGTG GTGATGGCGG TCATCCACGA TAGGCCGAAG AAACGCACCC    1500

CCATTCCTTT GATTCGTGTG GTGATGGATG ACAATGACAA GACTGTGCTA TTTGGTGTGT    1560

TTTACACCCA TGATGGGAGG TGGATGACTG TAATTCATAG TGGCGGTAGA CAAATACTTT    1620

CAACAGGGTG GGACCCAGAA AAACCGTGTC AGGTAGTGCT GCGACACGAC ACGGGCCATT    1680

GGGATTTCTA CGTTAACGCG AGGAAGGCTT ACTTTGGCAC CTACAAGGGT CTCTTCTCCA    1740

AACAAACAGT ATTTCACACA TCCAATTCCA CGGGAGAGT GGGGAAGTTG CAGAGTCCAG    1800

CCATTTGTCA CTCTTCAACG CCCGTTTGTA TAACCGAAGA CTCAATTCCA AGCATCTAAG    1860

ATGGCTCATG GTCGGCGAGA CAGGCCCAAA ATACGATGAT GGCAGCTCTT ATTCTGCGAG    1920

TGCGTCCGAG GAAGGAAGCA GAGGTGGCAG CTCCATGCCC GCGGGTACGT CCGAGGAAGG    1980

AAGCAGAGGT GGCAGCTCCA TGCCTGCGGG TACGTCCGAG GAAGGAAGCA GAGGAGGCAG    2040

CTCCATGCCT GCGGGTACGT CCGAGGAAGG AAGCAGAGGA GGCAGCTCCA TGCCTGCGGG    2100
```

-continued

```
TACGTCCGAG GAAGGAAGCA GAGGTGGCAG CTCCATGCCT GCGGGCACTT CCGAAGAAGG    2160

AAGCAGAAGT GGCANCTCCA TGCCTTCGGG CTCTTCCGAA GAAGGAAGCA GAAGAGGCCG    2220

CTCCCTGCCT TCGGGTTCTT CCGAAGGAAG GAAGCAGAGG AGGCCCTCCC TGCCTGCGGG    2280

TTCTTCCGAA GAAGGAAACA GAAGTGGCNC TCCATGCCCG CGGGTTCTTC CGAGGAAGGA    2340

ACCAGAAGAA GCNCTCCCTG CCCGCNGGTT CNTCCNAAGA AAGAAACANA AGTTGGCCNC    2400

TCCCNGCCCC NNGTTTCTTC CNAANGAAAG AAACAAAAGT GGCCCC                  2446
```

(2) INFORMATION FOR SEQ ID NO:18:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (xi) SEQUENCE DESCRIPTION: SEQ ID NO:18:

```
GGGTACGTCC GAGGAAGGAA GCAGAGGTGG CAGCTCCATG CCTGCGGGTA CGTCCGAGGA     60

AGGAAGCAGA GGTGTCAGCT CCATGCCTGC GGGTACGTCC GAGGAAGGAA ACAGAGGAGG    120

CAACTCCATG CCTGCGGGTA CGTCCGAGGA AGGAAGCAGA GGTGGCAGCT CCATGCCTTC    180

GGGCACGTCC GAGGAAGGAA GCAGAGGTGG CAGCTCCATG CCTTCGGGTA CGTCCGAGGA    240

AGGAAGCAGA GGAGGCAGCT CCATGCCTGC GGGTACGTCC GAGGAAGGAA GCAGAGGTGG    300

CAGCTCCATG CCCGCGGGTA CGTCCGAGGA AGGAAGCAGA GGCCG                    345
```

(2) INFORMATION FOR SEQ ID NO:19:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (xi) SEQUENCE DESCRIPTION: SEQ ID NO:19:

```
GGCACGAGCT GTACTATATT GTAGGAGAGC AGCCATGGGT ATCGTTCGCA GCCGCCTGCA     60

TAAACGCAAG ATCACCGGTG AAAGACGAA GATCCACCGG AAGCGCATGA AGGCCGAACT    120

CGGCCGTCTT CCCGCGCACA CGAAGCTTGG CGCCCGCCGC GTGAGTCCCG TCCGCGCCCG    180

CGGTGGGAAC TTCAAGCTCC GCGGTCTTCG CCTGGACACC GGCAATTTTG CGTGGAGCAC    240

AGAAGCCATT GCTCAGCGGG CCCGTATCCT CGACGTTGTG TACAACGCCA CTTCTAACGA    300

GCTGGTGCGC ACGAAGACGC TTGTGAAGAA CTGCATTGTT GTGGTGGACG CCGCGCCCTT    360

CAAGTTATGG TACGCGAAGC ACTACGGTAT CGACCTTGAG CCGCGAAGAG CAAGAAGACG    420

CTGCAGAGCA CGACGGAGAA GAAGAAGTCG AAGAAGACCT CACACGCCAT GACTGAGAAG    480

TACGACGTCA AGAAGGCCTC CGACGAGCTG AAGCGCAAGT GGATGCTCCG CCGCGAGAAC    540

CACAAGATTG AGAAGGCAGT TGCTGATCAG CTCAAGGAGG GCCGTCTGCT CGGCCGCATC    600

ACGAGCCGCC CTGGCCAGAC AGCCCGCGCC GATGGTGCAC TGCTGGAGGG CGCCGAACTG    660

CAGTTCTATC TGAAGAAGCT CGAGAAGAAG AAGCGGTAGA GAAGGATGTT CGGGAGACGG    720

GAGGAGGCGC CACCACCACC ACTCATGGTG ATGCACCCAC TACCTACTTT GTTTTCATTT    780

TTTGTTTTAC CTCTAATTTT TTAGGCCAGA GGGGGGAAA AAAAAAAAA AAAAA           835
```

(2) INFORMATION FOR SEQ ID NO:20:

(i) SEQUENCE CHARACTERISTICS:
        (A) LENGTH: 555 base pairs (B) TYPE: nucleic acid
    (C) STRANDEDNESS: single
    (D) TOPOLOGY: linear (xi) SEQUENCE DESCRIPTION: SEQ ID NO:20:

| | | | | | |
|---|---|---|---|---|---|
| GGCACGAGAA | AAAAGAAAAC | AAACAAATAA | AATCAAAAAC | AGTAAATCCA | TCACTTCAAC | 60 |
| AATGAGCATT | GAGAGCGCCT | TTTACGCCTT | TGCCTCCTTT | GGTGGTGCGC | CCACGAAAGA | 120 |
| GATGGACAAT | GCTCACTTCT | CCAAGATGCT | GAAGGAGACG | AAGGTCATTG | GAAAGCAATT | 180 |
| CACCAGCACC | GACGCCGATC | TTCTCTTCAA | CAAAGTGAAG | GCAAAGGGAG | CCCGCAAAAT | 240 |
| TACATTGTCG | GATTTTGTTG | ACAAGGCTGT | TCCTGAGATT | GCATCAAAGT | TAAAGAAGTC | 300 |
| CGCGGAGGAA | TTGATCGCAG | ATATTTCAAG | TTGCTCTCCC | GAGGCACGCG | CAACCAAGGC | 360 |
| CGATGCAGTT | AAGTTCCACG | ACGATAAGAA | CATGTACACT | GGTGTCTACA | AGGCCGGCGG | 420 |
| GCCAACAAAC | GTGGATCGCA | ACTCCGGCTC | CCTTTCAGGT | GTCGTGGATC | GCCGTGTGGC | 480 |
| GCAGACTGAC | GTTCGTGGCA | CGACTGCTTC | CCAGAAGTAA | AGAGGGAAAC | GAAATGGAAA | 540 |
| AAAAAAAAAA | AAAAA | | | | | 555 |

(2) INFORMATION FOR SEQ ID NO:21:

(i) SEQUENCE CHARACTERISTICS:
    (A) LENGTH: 936 base pairs
    (B) TYPE: nucleic acid
    (C) STRANDEDNESS: single
    (D) TOPOLOGY: linear (xi) SEQUENCE DESCRIPTION: SEQ ID NO:21:

| | | | | | |
|---|---|---|---|---|---|
| GGCACGAGAG | CTCTCTTCGT | CAGTCATGAC | GCTCGGGAAG | AACAAGCGCA | TCAGCAAGGG | 60 |
| CGGCAAGCGC | GGCAAGAAGA | AGACCCAGGA | GACGATGAGC | CGCAAGGAGT | GGTACGATGT | 120 |
| GGTTGCCCCC | AAGAACTTTG | AGGTGCGCCA | GTTTGGCAAG | ACCATCTGCA | ACAAGACCCA | 180 |
| GGGCACAAAG | ATCGCGGCGG | ACTACCTGCG | CGGGCGCGTG | TACGAAAGCA | ACCTTGCGGA | 240 |
| TCTGAACAAG | ACGCAAGGCG | ACGACGACGC | CTACCGCAAG | GTGAAGTTTG | TTGTGCAGGA | 300 |
| GGTGCAGGGC | CGCAACCTGC | TTACGCAGTT | CCACAGCATG | GAAATGACAT | CTGACCGCGT | 360 |
| GTACTTTTTG | CTGCGCAAGT | GGTGCACGAC | GATCGAGGCG | GCAGTGGAGA | CGAAGACTGC | 420 |
| GGACGGCTAC | ACCCTGCGCC | TCTTCGTGAT | TGCCTTCACG | AAGAAGCAGA | GCAACCAGCT | 480 |
| GTCGAAGAAC | TGCTATGCCA | AGACGCGCCT | GGTGAAGTGG | GTGCGCCATC | GCATCACGAA | 540 |
| CCTCATCCGC | CAGCGCCTGT | CGAAGGTGAA | CATCAACGAG | GCGGTGACGC | TGCTGACACG | 600 |
| CAACATCCTG | CGCGATCGTC | TGGCAAAGCG | CTGCAACCCC | ATCGTGCCGC | TGCGCGATCT | 660 |
| CCGCATCCGC | AAGGTGAAGG | TGGTCCGCAC | CCCCCGGTTT | TGACGCCCAG | GCGCTTCTGA | 720 |
| ATGCACACGG | CGAGATCCCC | GCCTCGGCTG | AGGGTGAGGC | ACGCGTCGTC | GAGGAAGCCC | 780 |
| AAGAGGCTCC | CGCCGCTGAA | GCCACAGCCT | AAGCCTTCCA | TGTGGAGGAA | GGATGTGTGA | 840 |
| TGTGAAAGCT | CTTTGTTCTT | TTTTCTTTCT | ATTTTGAAAC | GGTGATTCCG | CATATATATA | 900 |
| TTAAAAAAAA | AAAAAAAAAA | AAAAAAAAAA | AAAAA | | | 936 |

(2) INFORMATION FOR SEQ ID NO:22:

(i) SEQUENCE CHARACTERISTICS:
    (A) LENGTH: 581 base pairs
    (B) TYPE: nucleic acid
    (C) STRANDEDNESS: single
    (D) TOPOLOGY: linear (xi) SEQUENCE DESCRIPTION: SEQ ID NO:22:

```
GTACTATATT GTTGCTATTA ACACACTGTT AGGAACGCGA AACCATGCAG ATCTTCGTGA      60

AGACACTGAC GGGCAAGACG ATCGCGCTCG AGGTGGAATC CAGCGACACC ATTGAGAACG     120

TGAAGGCGAA GATCCAGGAC AAGGAGGGCA TTCCGCCGGA CCAGCAGCGC CTGATCTTCG     180

CTGGCAAGCA GCTGGAGGAC GGCCGCACGC TCGCAGACTA CAACATCCAG AAGGAGTCCA     240

CGCTGCACCT TGTGCTGCGC CTGCGCGGTG GTGTGATGGA GCCGACACTT GAGGCCCTGG     300

CGAAGAAGTA CAACTGGGAG AAGAAGGTAT GCCGCCGCTG CTACGCCCGT CTGCCGGTGC     360

GTGCGTCCAA CTGCCGCAAG AAGGCATGTG GCCACTGCTC CAACCTCCGC ATGAAGAAGA     420

AGCTGCGGTA GTCTGCGATG CTGTGGACCG ACGCATTGAA ATACACACCG TCTTCGGCGT     480

TCCTTTTTTT TATATGTCTT TTTTTTTATT GAGAAGATGT CTTGTTTGTT GTTGTTTTTT     540

TTTCAAAAAA AAAAAAAAAA AAAAAAAAAA AAAAAAAAAA A                        581
```

(2) INFORMATION FOR SEQ ID NO:23:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:23:

```
Leu Pro Pro Leu Leu Pro Ser Ser Asp Val Pro Glu Gly Met Glu Leu
1               5                   10                  15

Pro Pro Leu Leu Pro Ser Ser Asp Ile Pro Glu Gly Met Glu
            20                  25                  30
```

(2) INFORMATION FOR SEQ ID NO:24:

(i) SEQUENCE CHARACTERISTICS:
        (A) LENGTH: 90 amino acids
        (B) TYPE: amino acid
        (C) STRANDEDNESS:
        (D) TOPOLOGY: linear (xi) SEQUENCE DESCRIPTION: SEQ ID NO:24:

```
Gly Cys Leu Leu Cys Phe Leu Pro Arg Thr Cys Pro Lys Ala Trp Ser
1               5                   10                  15

Cys Leu Leu Cys Phe Leu Pro Arg Thr Tyr Pro Lys Ala Trp Ser Cys
            20                  25                  30

His Leu Cys Phe Leu Pro Arg Thr Tyr Pro Arg Ala Trp Ser Cys His
        35                  40                  45

Leu Cys Phe Leu Pro Arg Thr Cys Pro Lys Ala Trp Ser Cys His Leu
50                  55                  60

Cys Phe Leu Pro Arg Thr Tyr Pro Arg Ala Trp Ser Cys His Leu Cys
65                  70                  75                  80

Phe Leu Pro Arg Thr Tyr Pro Arg Val Trp
                85                  90
```

(2) INFORMATION FOR SEQ ID NO:25:

(i) SEQUENCE CHARACTERISTICS:
        (A) LENGTH: 90 amino acids
        (B) TYPE: amino acid
        (C) STRANDEDNESS:
        (D) TOPOLOGY: linear (xi) SEQUENCE DESCRIPTION: SEQ ID NO:25:

Ala Ala Ser Ser Ala Ser Phe Leu Gly Arg Ala Arg Arg His Gly Ala

-continued

```
1               5               10              15
Ala Ser Ser Ala Ser Phe Leu Gly His Thr Arg Arg His Gly Ala Ala
            20              25              30
Thr Ser Ala Ser Phe Leu Gly Arg Thr Arg Gly His Gly Ala Ala Thr
        35              40              45
Ser Ala Ser Phe Leu Gly Arg Ala Arg Arg His Gly Ala Ala Thr Ser
50              55              60
Ala Ser Phe Leu Gly Arg Thr Arg Gly His Gly Ala Ala Thr Ser Ala
65              70              75              80
Ser Phe Leu Gly Arg Thr Arg Gly His Gly
            85              90
```

(2) INFORMATION FOR SEQ ID NO:26:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:26:

```
Ser Val Pro Gly Lys Arg Leu Arg Asn Ser His Gly Lys Ser Leu Arg
1               5               10              15
Asn Val His Gly Lys Arg Pro Lys Asn Glu His Gly Lys Arg Leu Arg
            20              25              30
Ser Val Pro Asn Glu Arg Leu Arg
        35              40
```

(2) INFORMATION FOR SEQ ID NO:27:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:27:

```
Glu Ala Glu Glu Leu Ala Arg Gln Glu Ser Glu Glu Arg Ala Arg Gln
1               5               10              15
Glu Ala Glu Glu Arg Ala Trp Gln Glu Ala Glu Glu Arg Ala Gln Arg
            20              25              30
Glu Ala Glu Glu Arg Ala Gln Arg
        35              40
```

(2) INFORMATION FOR SEQ ID NO:28:

(i) SEQUENCE CHARACTERISTICS:
        (A) LENGTH: 56 amino acids
        (B) TYPE: amino acid
        (C) STRANDEDNESS:
        (D) TOPOLOGY: linear (xi) SEQUENCE DESCRIPTION: SEQ ID NO:28:

```
Ser Trp Gln Ser Gln Ser His Gln Gln Val Pro Thr Cys Ala Arg
1               5               10              15
Gln Ser Arg Ser His Gln Gln Ala Pro Lys Trp Ser Trp Gln Ser
            20              25              30
Gln Ser His Gln Gln Val Pro Thr Cys Ala Arg Gln Ser Arg Ser
        35              40              45
His Gln Gln Val Pro Thr Trp
50              55
```

(2) INFORMATION FOR SEQ ID NO:29:

(i) SEQUENCE CHARACTERISTICS:
        (A) LENGTH: 56 amino acids
        (B) TYPE: amino acid
        (C) STRANDEDNESS:
        (D) TOPOLOGY: linear (xi) SEQUENCE DESCRIPTION: SEQ ID NO:29:

```
Gly Arg Gly Arg Ala Lys Ala Thr Asn Ser Arg Cys Arg Arg Val Arg
1               5                  10                  15

Gly Arg Ala Glu Ala Thr Ser Ser Arg Arg Arg Ser Gly Arg Gly Arg
            20                  25                  30

Ala Lys Ala Thr Ser Ser Arg Cys Arg Pro Val Arg Gly Arg Ala Glu
        35                  40                  45

Ala Thr Asn Ser Arg Cys Arg Arg
    50                  55
```

(2) INFORMATION FOR SEQ ID NO:30:

(i) SEQUENCE CHARACTERISTICS:
        (A) LENGTH: 56 amino acids
        (B) TYPE: amino acid
        (C) STRANDEDNESS:
        (D) TOPOLOGY: linear (xi) SEQUENCE DESCRIPTION: SEQ ID NO:30:

```
Val Val Ala Glu Pro Lys Pro Pro Thr Ala Gly Ala Asp Val Cys Ala
1               5                  10                  15

Ala Glu Pro Lys Pro Pro Ala Ala Gly Ala Glu Val Val Val Ala Glu
            20                  25                  30

Pro Lys Pro Pro Ala Ala Gly Ala Asp Val Cys Ala Ala Glu Pro Lys
        35                  40                  45

Pro Pro Thr Ala Gly Ala Asp Val
    50                  55
```

(2) INFORMATION FOR SEQ ID NO:31:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:31:

```
Pro Pro Ala Lys Ala Ala Ala
1               5
```

(2) INFORMATION FOR SEQ ID NO:32:

(i) SEQUENCE CHARACTERISTICS:
        (A) LENGTH: 151 amino acids
        (B) TYPE: amino acid
        (C) STRANDEDNESS:
        (D) TOPOLOGY: linear (xi) SEQUENCE DESCRIPTION: SEQ ID NO:32:

```
Val Leu Gln Lys Glu Arg Asp Glu Ala Val Ala Glu Asn Ala Gln Leu
1               5                  10                  15

Gln Lys Glu Arg Asp Asp Ala Val Ala Glu Asn Ala Gln Leu Gln Lys
            20                  25                  30

Glu Arg Asp Asp Ala Val Ala Glu Asn Ala Gln Leu Gln Lys Glu Arg
```

-continued

```
                       35                  40                  45
Asp Asp Ala Val Ala Glu Asn Ala Gln Leu Gln Lys Glu Arg Asp Asp
     50                  55                  60

Ala Val Ala Glu Asn Ala Gln Leu Gln Lys Glu Arg Asp Glu Ala Val
 65                  70                  75                  80

Ala Glu Asn Ala Gln Leu Gln Arg Glu Arg Asp Asp Ala Val Ala Glu
                 85                  90                  95

Asp Ala Gln Leu Gln Lys Glu Arg Asp Glu Ala Val Ala Glu Asn Ala
                100                 105                 110

Gln Leu Gln Arg Glu Arg Asp Glu Ala Val Ala Glu Asn Ala Gln Leu
                115                 120                 125

Gln Lys Glu Arg Asp Asp Val Val Ala Glu Asn Ala Gln Leu Gln Lys
            130                 135                 140

Glu Arg Asp Asp Ala Val Ala
145                 150
```

(2) INFORMATION FOR SEQ ID NO:33:

(i) SEQUENCE CHARACTERISTICS:
        (A) LENGTH: 140 amino acids
        (B) TYPE: amino acid
        (C) STRANDEDNESS:
        (D) TOPOLOGY: linear (xi) SEQUENCE DESCRIPTION: SEQ ID NO:33:

```
Cys Arg Arg Arg Gly Met Lys Pro Trp Arg Arg Met Pro Ser Cys Arg
 1               5                  10                  15

Arg Arg Gly Met Thr Pro Trp Arg Arg Met Pro Ser Cys Arg Arg Arg
                20                  25                  30

Gly Met Thr Pro Trp Arg Arg Met Pro Ser Cys Arg Arg Arg Gly Met
                35                  40                  45

Thr Pro Trp Arg Arg Met Pro Ser Cys Arg Arg Arg Gly Met Thr Pro
             50                  55                  60

Trp Arg Arg Met Pro Ser Cys Arg Arg Arg Gly Thr Lys Pro Trp Arg
 65                  70                  75                  80

Arg Met Pro Ser Cys Arg Gly Arg Gly Met Thr Pro Trp Arg Arg Met
                 85                  90                  95

Pro Ser Cys Arg Arg Arg Gly Met Lys Pro Trp Arg Arg Met Pro Ser
                100                 105                 110

Cys Arg Gly Arg Gly Met Lys Pro Trp Arg Arg Met Pro Ser Cys Arg
            115                 120                 125

Arg Arg Gly Met Thr Ser Trp Arg Arg Met Pro Ser
            130                 135                 140
```

(2) INFORMATION FOR SEQ ID NO:34:

(i) SEQUENCE CHARACTERISTICS:
        (A) LENGTH: 60 amino acids
        (B) TYPE: amino acid
        (C) STRANDEDNESS:
        (D) TOPOLOGY: linear (xi) SEQUENCE DESCRIPTION: SEQ ID NO:34:

```
Gly Tyr Val Arg Gly Arg Lys Gln Arg Trp Gln Leu His Ala Phe Gly
 1               5                  10                  15

Tyr Val Arg Gly Arg Lys Gln Arg Trp Gln Leu His Ala Phe Gly Tyr
                20                  25                  30

Val Arg Gly Arg Lys Gln Arg Arg Gln Leu His Ala Cys Gly Tyr Val
```

```
                    35                  40                  45
Arg Gly Arg Lys Gln Arg Trp Gln Leu His Ala Cys
 50                  55                  60

(2) INFORMATION FOR SEQ ID NO:35:

(i) SEQUENCE CHARACTERISTICS:
        (A) LENGTH: 60 amino acids
        (B) TYPE: amino acid
        (C) STRANDEDNESS:
        (D) TOPOLOGY: linear (xi) SEQUENCE DESCRIPTION: SEQ ID NO:35:

Gly Thr Ser Glu Glu Gly Ser Arg Gly Gly Ser Ser Met Pro Ser Gly
 1               5                  10                  15

Thr Ser Glu Glu Gly Ser Arg Gly Gly Ser Ser Met Pro Ser Gly Thr
                20                  25                  30

Ser Glu Glu Gly Ser Arg Gly Gly Ser Ser Met Pro Ala Gly Thr Ser
            35                  40                  45

Glu Glu Gly Ser Arg Gly Gly Ser Ser Met Pro Ala
 50                  55                  60

(2) INFORMATION FOR SEQ ID NO:36:

(i) SEQUENCE CHARACTERISTICS:
        (A) LENGTH: 60 amino acids
        (B) TYPE: amino acid
        (C) STRANDEDNESS:
        (D) TOPOLOGY: linear (xi) SEQUENCE DESCRIPTION: SEQ ID NO:36:

Val Arg Pro Arg Lys Glu Ala Glu Val Ala Ala Pro Cys Leu Arg Val
 1               5                  10                  15

Arg Pro Arg Lys Glu Ala Glu Val Ala Ala Pro Cys Leu Arg Val Arg
                20                  25                  30

Pro Arg Lys Glu Ala Glu Val Ala Ala Pro Cys Leu Arg Val Arg Pro
            35                  40                  45

Arg Lys Glu Ala Glu Val Ala Ala Pro Cys Leu Arg
 50                  55                  60

(2) INFORMATION FOR SEQ ID NO:37:

(i) SEQUENCE CHARACTERISTICS:
        (A) LENGTH: 639 amino acids
        (B) TYPE: amino acid
        (C) STRANDEDNESS:
        (D) TOPOLOGY: linear (xi) SEQUENCE DESCRIPTION: SEQ ID NO:37:

Asp Ala Ser Val Val Asp Leu Gly Gly Glu Ala His Gly Thr His Tyr
 1               5                  10                  15

Ala Phe Leu Pro Asp Val Ile Lys Gly Ile Ala Gln Glu Glu Leu Tyr
                20                  25                  30

Leu Glu Asp Asp Ala Tyr Phe Gln Glu Leu Leu Ala Arg Tyr Lys Glu
            35                  40                  45

Leu Val Pro Val Gly Ala Glu Pro Thr Glu Pro Arg Ala Lys Gln Leu
 50                  55                  60

Arg Glu Gln Met Arg Ile Arg Ala Gly Gln Leu Ala Val Asp Thr Arg
 65                  70                  75                  80

Lys Leu His Ala Ala Glu Glu Arg Ala Ala Ser Arg Met Ala Thr Leu
                85                  90                  95
```

```
Tyr Pro Phe Val Gly Ser Ala Pro Leu Gly Val Ala Leu Trp Asn Ile
            100                 105                 110

Pro Val Glu Ala Asp Glu Glu Phe Cys Ala Leu Leu Leu Lys Arg Glu
            115                 120                 125

Glu Ala Leu Ala Gly Lys Ser Gly Ser Val His Glu Val Glu Ser Ala
        130                 135                 140

Leu Ser Ala Arg Ala Glu Ala Met Ala Lys Ala Val Leu Glu Glu Glu
145                 150                 155                 160

Glu Ala Leu Ala Ala Ala Phe Pro Phe Leu Gly Arg Ser Val Lys Gly
                165                 170                 175

Ala Pro Leu Arg Glu Leu Ala Leu Met Ser Asp Pro Asn Phe Ala Glu
            180                 185                 190

Leu Ala Thr Arg His Ala Gln Glu Ala Thr Ser Gly Asp Ala Ala Gly
            195                 200                 205

Ile Leu Arg Leu Glu Gln Glu Leu Arg Asp Gln Ala Cys Arg Ile Ala
        210                 215                 220

Arg Glu Val Arg Val Ala Arg Arg Leu Asp Ala Xaa Arg Asn Glu Asp
225                 230                 235                 240

Leu His Glu Arg Tyr Pro Phe Leu Pro Glu Glu Pro Val Arg Gly Ile
                245                 250                 255

Leu Leu Gly Ala Val Arg Pro Val Gln Gln Pro Ala Phe Arg Glu Leu
            260                 265                 270

Ser Asn Lys Leu Asp Glu Gln Arg Arg Asp Pro Thr Arg Asn Ala Ala
        275                 280                 285

Ala Ile Arg Thr Thr Glu Glu Gln Met Thr Ala Leu Val Val Arg Leu
290                 295                 300

Ala Glu Glu Arg Ala Glu Ala Thr Glu Arg Ala His Glu Gln Tyr Pro
305                 310                 315                 320

Phe Leu Pro Arg Arg Val Leu Gly Val Arg Leu Gly Asp Ile Ser Leu
                325                 330                 335

Gln Glu Asp Asp Val Leu Ser Gln Leu Ala Arg Arg Val Arg Gln
            340                 345                 350

Leu Arg Asn Ser Lys Thr Ala Ile Asp Ala His Ala Thr Glu Glu Glu
        355                 360                 365

Met Ile Arg Arg Ala Glu Glu Leu Ala Arg Asn Val Lys Leu Val Asp
370                 375                 380

Ala Tyr Arg Gly Asn Gly Asn Glu Tyr Val Arg Ala Cys Asn Pro Phe
385                 390                 395                 400

Leu Val Tyr Glu Asp Arg Lys Cys Val Leu Leu Ser Glu Leu Pro Leu
                405                 410                 415

Ala Gly Gly Asp Val Tyr Gln Gly Leu Phe Arg Asp Tyr Leu Thr Ala
            420                 425                 430

Leu Glu Asp Ala Glu Ala Asn Ala Pro Arg Ile Ala Glu Leu Glu Asn
        435                 440                 445

Ala Leu Arg Ser Arg Ala Asp Gly Leu Ala Leu Glu Val Cys Glu Arg
    450                 455                 460

Asp Ala Arg Leu Leu His Tyr Ser Phe Leu Ser Ala Gln Asp Val Pro
465                 470                 475                 480

Gly Trp Ser Glu Ala Leu Leu His Asp Ala Glu Phe Gln Gln Leu Arg
                485                 490                 495

Glu Arg Tyr Glu Glu Leu Ser Lys Asp Pro Gln Gly Asn Ala Glu Ala
            500                 505                 510
```

```
Leu Arg Glu Leu Glu Asp Ala Met Glu Ala Arg Ser Arg Ala Ile Ala
            515                 520                 525

Glu Ala Leu Arg Thr Ala Glu Xaa Thr Asn Xaa Thr Glu Gln Ala Arg
        530                 535                 540

Leu Lys Thr Pro Ser Gln Ala Gly Ser Gly Val Ser Ala Gly Asp Arg
545                 550                 555                 560

Met His Gly Ser Glu His Ala Asp Leu Ala His Glu Gly Gly Ser Thr
                565                 570                 575

Ala Gly Gly Thr Met Arg Gly Ala Glu Ser Val Ser Lys Ser Ser Gly
            580                 585                 590

Lys His Ser Xaa Arg Ser Val Ser His Ala Ser Val Val Asp Leu Gly
                595                 600                 605

Gly Glu Ala His Gly Thr His Tyr Ala Phe Leu Pro Asp Val Ile Lys
        610                 615                 620

Gly Ile Ala Gln Glu Glu Leu Tyr Leu Glu Asp Asp Ala Tyr Phe
625                 630                 635

(2) INFORMATION FOR SEQ ID NO:38:

(i) SEQUENCE CHARACTERISTICS:
        (A) LENGTH: 231 amino acids
        (B) TYPE: amino acid
        (C) STRANDEDNESS:
        (D) TOPOLOGY: linear (xi) SEQUENCE DESCRIPTION: SEQ ID NO:38:

Ala Arg Ala Val Leu Tyr Cys Arg Arg Ala Ala Met Gly Ile Val Arg
1               5                   10                  15

Ser Arg Leu His Lys Arg Lys Ile Thr Gly Gly Lys Thr Lys Ile His
            20                  25                  30

Arg Lys Arg Met Lys Ala Glu Leu Gly Arg Leu Pro Ala His Thr Lys
            35                  40                  45

Leu Gly Ala Arg Arg Val Ser Pro Val Arg Ala Arg Gly Gly Asn Phe
    50                  55                  60

Lys Leu Arg Gly Leu Arg Leu Asp Thr Gly Asn Phe Ala Trp Ser Thr
65                  70                  75                  80

Glu Ala Ile Ala Gln Arg Ala Arg Ile Leu Asp Val Val Tyr Asn Ala
                85                  90                  95

Thr Ser Asn Glu Leu Val Arg Thr Lys Thr Leu Val Lys Asn Cys Ile
            100                 105                 110

Val Val Val Asp Ala Ala Pro Phe Lys Leu Trp Tyr Ala Lys His Tyr
        115                 120                 125

Gly Ile Asp Leu Asp Ala Ala Lys Ser Lys Thr Leu Gln Ser Thr
    130                 135                 140

Thr Glu Lys Lys Lys Ser Lys Lys Thr Ser His Ala Met Thr Glu Lys
145                 150                 155                 160

Tyr Asp Val Lys Lys Ala Ser Asp Glu Leu Lys Arg Lys Trp Met Leu
                165                 170                 175

Arg Arg Glu Asn His Lys Ile Glu Lys Ala Val Ala Asp Gln Leu Lys
            180                 185                 190

Glu Gly Arg Leu Leu Ala Arg Ile Thr Ser Arg Pro Gly Thr Ala Arg
        195                 200                 205

Ala Asp Gly Ala Leu Leu Glu Gly Ala Glu Leu Gln Phe Tyr Leu Lys
    210                 215                 220

Lys Leu Glu Lys Lys Lys Arg
225                 230
```

(2) INFORMATION FOR SEQ ID NO:39:

(i) SEQUENCE CHARACTERISTICS:
        (A) LENGTH: 172 amino acids
        (B) TYPE: amino acid
        (C) STRANDEDNESS:
        (D) TOPOLOGY: linear (xi) SEQUENCE DESCRIPTION: SEQ ID NO:39:

```
Ala Arg Glu Lys Arg Lys Gln Thr Asn Lys Ile Lys Asn Ser Lys Ser
1               5                   10                  15

Ile Thr Ser Thr Met Ser Glu Glu Ser Ala Phe Tyr Ala Phe Ala Ser
            20                  25                  30

Phe Gly Gly Ala Pro Thr Lys Glu Met Asp Asn Ala His Phe Ser Lys
        35                  40                  45

Met Leu Lys Glu Thr Lys Val Ile Gly Lys Gln Phe Thr Ser Thr Asp
    50                  55                  60

Ala Asp Leu Leu Phe Asn Lys Val Lys Ala Lys Gly Ala Arg Lys Ile
65                  70                  75                  80

Thr Leu Ser Asp Phe Val Asp Lys Ala Val Pro Glu Ile Ala Ser Lys
                85                  90                  95

Leu Lys Lys Ser Ala Glu Glu Leu Ile Ala Asp Ile Ser Ser Cys Ser
            100                 105                 110

Pro Glu Ala Arg Ala Thr Lys Ala Asp Ala Val Lys Phe His Asp Asp
        115                 120                 125

Lys Asn Met Tyr Thr Gly Val Tyr Lys Ala Gly Pro Thr Asn Val
    130                 135                 140

Asp Arg Asn Ser Gly Ser Leu Ser Gly Val Val Asp Arg Arg Val Ala
145                 150                 155                 160

Gln Thr Asp Val Arg Gly Thr Thr Ala Ser Gln Lys
                165                 170
```

(2) INFORMATION FOR SEQ ID NO:40:

(i) SEQUENCE CHARACTERISTICS:
        (A) LENGTH: 233 amino acids
        (B) TYPE: amino acid
        (C) STRANDEDNESS:
        (D) TOPOLOGY: linear (xi) SEQUENCE DESCRIPTION: SEQ ID NO:40:

```
Ala Arg Glu Leu Ser Ser Ser Val Met Thr Leu Gly Lys Asn Lys Arg
1               5                   10                  15

Ile Ser Lys Gly Gly Lys Arg Gly Lys Lys Thr Gln Glu Thr Met
            20                  25                  30

Ser Arg Lys Glu Trp Tyr Asp Val Val Ala Pro Lys Asn Phe Glu Val
        35                  40                  45

Arg Gln Phe Gly Lys Thr Ile Cys Asn Lys Thr Gln Gly Thr Lys Ile
    50                  55                  60

Ala Ala Asp Tyr Leu Arg Gly Arg Val Tyr Glu Ser Asn Leu Ala Asp
65                  70                  75                  80

Leu Asn Lys Thr Gln Gly Asp Asp Ala Tyr Arg Lys Val Lys Phe
                85                  90                  95

Val Val Gln Glu Val Gln Gly Arg Asn Leu Leu Thr Gln Phe His Ser
            100                 105                 110

Met Glu Met Thr Ser Asp Arg Val Tyr Phe Leu Leu Arg Lys Trp Cys
        115                 120                 125
```

```
Thr Thr Ile Glu Ala Ala Val Glu Thr Lys Thr Ala Asp Gly Tyr Thr
    130                 135                 140

Leu Arg Leu Phe Val Ile Ala Phe Thr Lys Lys Gln Ser Asn Gln Leu
145                 150                 155                 160

Ser Lys Asn Cys Tyr Ala Lys Thr Arg Leu Val Lys Trp Val Arg His
                165                 170                 175

Arg Ile Thr Asn Leu Ile Arg Gln Arg Leu Ser Lys Val Asn Ile Asn
            180                 185                 190

Glu Ala Val Thr Leu Leu Thr Arg Asn Ile Leu Arg Asp Arg Leu Ala
        195                 200                 205

Lys Arg Cys Asn Pro Ile Val Pro Leu Arg Asp Leu Arg Ile Arg Lys
    210                 215                 220

Val Lys Val Val Arg Thr Pro Arg Phe
225                 230

(2) INFORMATION FOR SEQ ID NO:41:

(i) SEQUENCE CHARACTERISTICS:
        (A) LENGTH: 128 amino acids
        (B) TYPE: amino acid
        (C) STRANDEDNESS:
        (D) TOPOLOGY: linear (xi) SEQUENCE DESCRIPTION: SEQ ID NO:41:

Met Gln Ile Phe Val Lys Thr Leu Thr Gly Lys Thr Ile Ala Leu Glu
1               5                   10                  15

Val Glu Ser Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Val Met Glu Pro
65                  70                  75                  80

Thr Leu Glu Ala Leu Ala Lys Lys Tyr Asn Trp Glu Lys Lys Val Cys
                85                  90                  95

Arg Arg Cys Tyr Ala Arg Leu Pro Val Arg Ala Ser Asn Cys Arg Lys
            100                 105                 110

Lys Ala Cys Gly His Cys Ser Asn Leu Arg Met Lys Lys Lys Leu Arg
        115                 120                 125

(2) INFORMATION FOR SEQ ID NO:42:

(i) SEQUENCE CHARACTERISTICS:
        (A) LENGTH: 145 amino acids
        (B) TYPE: amino acid
        (C) STRANDEDNESS:
        (D) TOPOLOGY: linear (xi) SEQUENCE DESCRIPTION: SEQ ID NO:42:

Arg Leu Pro Pro Leu Leu Pro Ser Ser Asp Val Pro Glu Gly Met Glu
1               5                   10                  15

Leu Pro Pro Leu Leu Pro Ser Ser Asp Ile Pro Glu Gly Met Glu Leu
            20                  25                  30

Pro Pro Leu Leu Pro Ser Ser Asp Val Pro Ala Gly Met Glu Leu Thr
        35                  40                  45

Pro Leu Leu Pro Ser Ser Asp Val Pro Glu Gly Met Glu Leu Pro Pro
    50                  55                  60
```

Leu Leu Pro Ser Ser Asp Val Pro Ala Gly Met Glu Leu Pro Pro Leu
65                  70                  75                  80

Xaa Pro Ser Ser Asp Val Pro Ala Gly Met Glu Leu Pro Pro Leu Leu
                85                  90                  95

Pro Ser Ser Asp Val Pro Ala Xaa Ile Glu Leu Pro Pro Leu Ile Ser
            100                 105                 110

Xaa Leu Gly Arg Thr Xaa Arg Xaa Gly Asp Xaa Ser Ser Xaa Ser Cys
        115                 120                 125

Leu Gly Arg Xaa Xaa Arg Xaa Arg Xaa Ala Pro Leu Xaa Pro Xaa Ser
    130                 135                 140

Glu
145

(2) INFORMATION FOR SEQ ID NO:43:

(i) SEQUENCE CHARACTERISTICS:
        (A) LENGTH: 186 amino acids
        (B) TYPE: amino acid
        (C) STRANDEDNESS:
        (D) TOPOLOGY: linear (xi) SEQUENCE DESCRIPTION: SEQ ID NO:43:

Glu Lys Glu Arg Arg Phe Pro Thr Lys Thr Ala Arg Ala Asp Pro Thr
1               5                   10                  15

Thr Thr Lys Gln Leu Ile Ile Arg Ala Leu Gln Asn Ile Ser Leu Ala
                20                  25                  30

Phe Gly Ile Glu Pro Ser Ser Thr Val Lys Tyr Ala Glu Ser Thr Gln
            35                  40                  45

Glu Glu Asn Gly Lys Arg Ser Gln Ser Glu Ala Glu Glu Arg Ala Arg
50                  55                  60

Arg Glu Ala Glu Arg Ala Arg Arg Glu Ala Glu Glu Arg Ala Gln
65                  70                  75                  80

Arg Glu Ala Glu Glu Arg Ala Gln Arg Glu Ala Glu Glu Arg Ala Arg
                85                  90                  95

Arg Glu Ala Glu Lys Arg Ala Arg Arg Glu Ala Lys Glu Arg Ala Trp
            100                 105                 110

Gln Glu Ala Glu Glu Arg Ala Gln Arg Glu Ala Glu Glu Arg Ala Arg
        115                 120                 125

Arg Glu Ala Glu Glu Arg Ala Arg Arg Glu Val Glu Glu Arg Ala Arg
    130                 135                 140

Gln Glu Ala Glu Glu Leu Ala Arg Gln Glu Ser Glu Glu Arg Ala Arg
145                 150                 155                 160

Gln Glu Ala Glu Glu Arg Ala Trp Gln Glu Ala Glu Glu Arg Ala Gln
                165                 170                 175

Arg Glu Ala Glu Glu Arg Ala Gln Arg Ala
            180                 185

(2) INFORMATION FOR SEQ ID NO:44:

(i) SEQUENCE CHARACTERISTICS:
        (A) LENGTH: 106 amino acids
        (B) TYPE: amino acid
        (C) STRANDEDNESS:
        (D) TOPOLOGY: linear (xi) SEQUENCE DESCRIPTION: SEQ ID NO:44:

Gly Arg Gly Arg Ala Lys Ala Thr Asn Ser Arg Cys Arg Arg Val Arg
1               5                   10                  15

```
Gly Arg Ala Glu Ala Thr Ser Ser Arg Arg Ser Gly Arg Gly Arg
             20                  25                  30

Ala Lys Ala Thr Ser Ser Arg Cys Arg Arg Val Arg Gly Arg Val Glu
             35                  40                  45

Ala Thr Asn Ser Arg Cys Arg Arg Gly Arg Gly Arg Ala Lys Val Thr
             50                  55                  60

Ser Ser Arg Xaa Arg Arg Val Xaa Gly Arg Xaa Xaa Xaa Thr Ser Xaa
65                   70                  75                  80

Arg Xaa Arg Arg Xaa Arg Gly Arg Xaa Xaa Val Thr Ser Arg Arg Xaa
                 85                  90                  95

Arg Arg Xaa Xaa Gly Arg Gly Asp Val Thr
             100                 105
```

(2) INFORMATION FOR SEQ ID NO:45:

(i) SEQUENCE CHARACTERISTICS:
        (A) LENGTH: 141 amino acids
        (B) TYPE: amino acid
        (C) STRANDEDNESS:
        (D) TOPOLOGY: linear (xi) SEQUENCE DESCRIPTION: SEQ ID NO:45:

```
Ser Ile Pro Val Glu Ile Asp Ile Arg Asn Gln Asp Phe Ser Phe Leu
1                5                  10                  15

Asp Pro Ala Pro Glu Gly Ile Pro Ile Gln Asp Ile His Leu Met Gly
             20                  25                  30

Asp Ser Ala Phe Ala Ala Ser Ala Arg Glu Arg Met Lys Leu Lys Arg
             35                  40                  45

Asn Pro Val Ala Asn Ala Ser Lys Ile Ser Ala Leu Glu Glu Glu Met
             50                  55                  60

Asp Gln Arg Ala His Val Leu Ala Lys Gln Val Arg Asp Lys Glu Arg
65                   70                  75                  80

Thr Phe Leu Asp Pro Glu Pro Glu Gly Val Pro Leu Glu Leu Leu Ser
                 85                  90                  95

Leu Asn Glu Asn Glu Ala Ser Gln Glu Leu Glu Arg Glu Leu Arg Ala
             100                 105                 110

Leu Asn Arg Lys Pro Arg Lys Asp Ala Lys Ala Ile Val Ala Leu Glu
             115                 120                 125

Asp Asp Val Arg Asp Glu His Thr Cys Leu Pro Arg Ser
             130                 135                 140
```

(2) INFORMATION FOR SEQ ID NO:46:

(i) SEQUENCE CHARACTERISTICS:
        (A) LENGTH: 27 amino acids
        (B) TYPE: amino acid
        (C) STRANDEDNESS:
        (D) TOPOLOGY: linear (xi) SEQUENCE DESCRIPTION: SEQ ID NO:46:

```
Arg Lys Met Ser Gly Thr Ser Leu Leu Ala Pro Gln Pro Glu Gly Val
1                5                  10                  15

Pro Val Ser Glu Leu Ser Leu Asp Leu Asp Glu
             20                  25
```

(2) INFORMATION FOR SEQ ID NO:47:

(i) SEQUENCE CHARACTERISTICS:
        (A) LENGTH: 117 amino acids (B) TYPE: amino acid
        (C) STRANDEDNESS:
        (D) TOPOLOGY: linear (xi) SEQUENCE DESCRIPTION: SEQ ID NO:47:

Leu Leu Ala Leu Leu Gln Gly Leu Val Gln Leu Arg Thr Gln Ile His
1               5                  10                  15

Gly Val Arg Pro Ala Leu Leu Pro Glu Ser Gly Gln Phe Leu Gly Gly
                20                  25                  30

Ser Leu Gln Leu Ala Met His Leu Leu Ala Leu Leu Gln Gly Leu Val
            35                  40                  45

Gln Leu Arg Thr Gln Ile His Gly Val Arg Pro Ala Leu Leu Pro Glu
        50                  55                  60

Ser Gly Gln Phe Leu Gly Gly Ser Leu Gln Leu Ala Met His Leu Leu
65                  70                  75                  80

Ala Leu Leu Gln Gly Leu Val Gln Leu Arg Thr Gln Ile His Gly Val
                85                  90                  95

Arg Pro Ala Leu Leu Pro Glu Ser Gly Gln Phe Leu Gly Gly Ser Leu
                100                 105                 110

Gln Leu Ala Thr His
        115

(2) INFORMATION FOR SEQ ID NO:48:

(i) SEQUENCE CHARACTERISTICS:
        (A) LENGTH: 117 amino acids
        (B) TYPE: amino acid
        (C) STRANDEDNESS:
        (D) TOPOLOGY: linear (xi) SEQUENCE DESCRIPTION: SEQ ID NO:48:

Ser Ser Arg Cys Cys Lys Ala Ser Ser Cys Ala Arg Arg Phe Thr
1               5                  10                  15

Val Ser Ala Pro Leu Cys Ser Arg Arg Ala Ala Ser Ser Ser Val Val
                20                  25                  30

Arg Phe Ser Ser Arg Cys Thr Ser Ser Arg Cys Cys Lys Ala Ser Ser
            35                  40                  45

Ser Cys Ala Arg Arg Phe Thr Val Ser Ala Pro Leu Cys Ser Arg Arg
        50                  55                  60

Ala Gly Ser Ser Ser Val Val Arg Phe Ser Ser Arg Cys Thr Ser Ser
65                  70                  75                  80

Arg Cys Cys Lys Ala Ser Ser Ser Cys Ala Arg Arg Phe Thr Val Ser
                85                  90                  95

Ala Pro Leu Cys Ser Arg Arg Ala Gly Ser Ser Ser Val Val Arg Phe
                100                 105                 110

Ser Ser Arg Arg Thr
        115

(2) INFORMATION FOR SEQ ID NO:49:

(i) SEQUENCE CHARACTERISTICS:
        (A) LENGTH: 117 amino acids
        (B) TYPE: amino acid
        (C) STRANDEDNESS:
        (D) TOPOLOGY: linear (xi) SEQUENCE DESCRIPTION: SEQ ID NO:49:

Pro Pro Arg Ala Ala Ala Arg Pro Arg Pro Ala Ala His Ala Asp Ser
1               5                  10                  15

```
Arg Cys Pro Pro Arg Ser Ala Pro Gly Glu Arg Pro Val Pro Arg Trp
             20                  25                  30

Phe Ala Ser Ala Arg Asp Ala Pro Arg Ala Ala Arg Pro Arg
         35                  40                  45

Pro Ala Ala His Ala Asp Ser Arg Cys Pro Pro Arg Ser Ala Pro Gly
         50                  55                  60

Glu Arg Ala Val Pro Arg Trp Phe Ala Ser Ala Arg Asp Ala Pro Pro
 65                  70                  75                  80

Arg Ala Ala Ala Arg Pro Arg Pro Ala Ala His Ala Asp Ser Arg Cys
                 85                  90                  95

Pro Pro Arg Ser Ala Pro Gly Glu Arg Ala Val Pro Arg Trp Phe Ala
                100                 105                 110

Ser Ala Arg Asp Ala
            115

(2) INFORMATION FOR SEQ ID NO:50:

(i) SEQUENCE CHARACTERISTICS:
        (A) LENGTH: 207 amino acids
        (B) TYPE: amino acid
        (C) STRANDEDNESS:
        (D) TOPOLOGY: linear (xi) SEQUENCE DESCRIPTION: SEQ ID NO:50:

Ala Glu Pro Lys Pro Ala Glu Pro Lys Ser Ala Glu Pro Lys Pro Ala
 1               5                  10                  15

Glu Pro Lys Ser Ala Glu Pro Lys Pro Ala Glu Pro Lys Ser Ala Glu
                 20                  25                  30

Pro Lys Pro Ala Glu Pro Lys Ser Ala Gly Pro Lys Pro Ala Glu Pro
             35                  40                  45

Lys Ser Ala Glu Pro Lys Pro Ala Glu Pro Lys Ser Ala Glu Pro Lys
 50                  55                  60

Pro Ala Glu Pro Lys Ser Ala Glu Pro Lys Pro Ala Glu Pro Lys Ser
 65                  70                  75                  80

Ala Glu Pro Lys Pro Ala Glu Ser Lys Ser Ala Glu Pro Lys Pro Ala
                 85                  90                  95

Glu Pro Lys Ser Ala Glu Pro Lys Pro Ala Glu Ser Lys Ser Ala Glu
                100                 105                 110

Pro Lys Pro Ala Glu Pro Lys Ser Ala Glu Pro Lys Pro Ala Glu Pro
            115                 120                 125

Lys Ser Ala Glu Pro Lys Pro Ala Glu Pro Lys Ser Ala Glu Pro Lys
130                 135                 140

Pro Ala Glu Pro Lys Ser Ala Glu Pro Lys Pro Ala Glu Ser Lys Ser
145                 150                 155                 160

Ala Gly Pro Lys Pro Ala Glu Pro Lys Ser Ala Glu Pro Lys Pro Ala
                165                 170                 175

Glu Pro Lys Ser Ala Glu Pro Lys Pro Ala Glu Pro Lys Ser Ala Glu
                180                 185                 190

Pro Lys Pro Ala Glu Pro Lys Ser Ala Glu Pro Lys Pro Ala Glu
            195                 200                 205

(2) INFORMATION FOR SEQ ID NO:51:

(i) SEQUENCE CHARACTERISTICS:
        (A) LENGTH: 263 amino acids
        (B) TYPE: amino acid
        (C) STRANDEDNESS:
        (D) TOPOLOGY: linear
```

(xi) SEQUENCE DESCRIPTION: SEQ ID NO:51:

```
Arg Arg Gly Tyr Pro Arg Ser Arg Met Pro Ser Lys Glu Leu Trp Met
1               5                   10                  15

Arg Arg Leu Arg Ile Leu Arg Arg Leu Leu Arg Lys Tyr Arg Glu Glu
            20                  25                  30

Lys Lys Ile Asp Arg His Ile Tyr Arg Glu Leu Tyr Val Lys Ala Lys
            35                  40                  45

Gly Asn Val Phe Arg Asn Lys Arg Asn Leu Met Glu His Ile His Lys
        50                  55                  60

Val Lys Asn Glu Lys Lys Lys Glu Arg Gln Leu Ala Glu Gln Leu Ala
65                  70                  75                  80

Ala Asn Ala Xaa Lys Asp Glu Gln His Arg His Lys Ala Arg Lys Gln
                85                  90                  95

Glu Leu Arg Lys Arg Glu Lys Asp Arg Glu Arg Ala Arg Arg Glu Asp
            100                 105                 110

Ala Ala Ala Ala Ala Ala Lys Gln Lys Ala Ala Ala Lys Lys Ala
            115                 120                 125

Ala Ala Pro Ser Gly Lys Lys Ser Ala Lys Ala Ala Ile Ala Pro Ala
    130                 135                 140

Lys Ala Ala Ala Ala Pro Ala Lys Ala Ala Ala Ala Pro Ala Lys Ala
145                 150                 155                 160

Ala Ala Ala Pro Ala Lys Ala Ala Ala Pro Ala Lys Ala Ala Ala
            165                 170                 175

Ala Pro Ala Lys Ala Ala Thr Ala Pro Ala Lys Ala Ala Ala Ala Pro
        180                 185                 190

Ala Lys Thr Ala Ala Ala Pro Ala Lys Ala Ala Ala Pro Ala Lys Ala
        195                 200                 205

Ala Ala Ala Pro Ala Lys Ala Ala Thr Ala Pro Ala Lys Ala Ala Ala
            210                 215                 220

Ala Pro Ala Lys Ala Ala Thr Ala Pro Ala Lys Ala Ala Thr Ala Pro
225                 230                 235                 240

Ala Lys Ala Ala Ala Ala Pro Ala Lys Ala Ala Thr Ala Pro Val Gly
                245                 250                 255

Lys Lys Ala Gly Gly Lys Lys
            260
```

(2) INFORMATION FOR SEQ ID NO:52:

(i) SEQUENCE CHARACTERISTICS:
        (A) LENGTH: 442 amino acids
        (B) TYPE: amino acid
        (C) STRANDEDNESS:
        (D) TOPOLOGY: linear (xi) SEQUENCE DESCRIPTION: SEQ ID NO:52:

```
Asp Phe Ile Trp Tyr Lys Val Val Ala Leu Leu Val Val Ile Thr Ser
1               5                   10                  15

Asn Gly Asp Asp Val Ser Val Tyr Thr Ala Thr Ile Lys Glu Phe Tyr
            20                  25                  30

Arg Tyr Leu Trp Ile Phe Val Pro Val Ser Leu Phe Ser Ile Ile Ile
            35                  40                  45

Tyr Phe Val Ser Ile Phe Cys Phe Pro Ala Ser Tyr Gly Leu Phe Phe
        50                  55                  60

Ser Ser Phe Leu Lys Phe Gln Leu Leu Leu Asn His Lys His Pro Val
65                  70                  75                  80
```

```
Leu Gln Pro Pro His Gln Met Val Ser Leu Lys Leu Gln Ala Arg Leu
                 85                  90                  95

Ala Ala Asp Ile Leu Arg Cys Gly Arg His Arg Val Trp Leu Asp Pro
            100                 105                 110

Asn Glu Ala Ser Glu Ile Ser Asn Ala Asn Ser Arg Lys Ser Val Arg
            115                 120                 125

Lys Leu Ile Lys Asp Gly Leu Ile Ile Arg Lys Pro Val Lys Val His
            130                 135                 140

Ser Arg Ser Arg Trp Arg His Met Lys Glu Ala Lys Ser Met Gly Arg
145                 150                 155                 160

His Glu Gly Ala Gly Arg Arg Glu Gly Thr Arg Glu Ala Arg Met Pro
                165                 170                 175

Ser Lys Glu Leu Trp Met Arg Arg Leu Arg Ile Leu Arg Arg Leu Leu
                180                 185                 190

Arg Lys Tyr Arg Glu Glu Lys Lys Ile Asp Arg His Ile Tyr Arg Glu
            195                 200                 205

Leu Tyr Val Lys Ala Lys Gly Asn Val Phe Arg Asn Lys Arg Asn Leu
    210                 215                 220

Met Glu His Ile His Lys Val Lys Asn Glu Lys Lys Lys Glu Arg Gln
225                 230                 235                 240

Leu Ala Glu Gln Leu Ala Ala Lys Arg Leu Lys Asp Glu Gln His Arg
                245                 250                 255

His Lys Ala Arg Lys Gln Glu Leu Arg Lys Arg Glu Lys Asp Arg Glu
            260                 265                 270

Arg Ala Arg Arg Glu Asp Ala Ala Ala Ala Ala Lys Gln Lys
            275                 280                 285

Ala Ala Ala Lys Lys Ala Ala Ala Pro Ser Gly Lys Lys Ser Ala Lys
    290                 295                 300

Ala Ala Ala Pro Ala Lys Ala Ala Ala Pro Ala Lys Ala Ala Ala
305                 310                 315                 320

Pro Pro Ala Lys Thr Ala Ala Pro Ala Lys Ala Ala Ala Pro Ala
                325                 330                 335

Lys Ala Ala Ala Pro Pro Ala Lys Ala Ala Ala Pro Pro Ala Lys Thr
            340                 345                 350

Ala Ala Pro Pro Ala Lys Thr Ala Ala Pro Ala Lys Ala Ala Ala
                355                 360                 365

Pro Pro Ala Lys Ala Ala Ala Pro Pro Ala Lys Ala Ala Ala Pro Pro
    370                 375                 380

Ala Lys Ala Ala Ala Ala Pro Ala Lys Ala Ala Ala Pro Ala Lys
385                 390                 395                 400

Ala Ala Ala Pro Pro Ala Lys Ala Ala Ala Pro Pro Ala Lys Ala Ala
                405                 410                 415

Ala Pro Pro Ala Lys Ala Ala Ala Pro Pro Ala Lys Ala Ala Ala Ala
            420                 425                 430

Pro Val Gly Lys Lys Ala Gly Gly Lys Lys
            435                 440

(2) INFORMATION FOR SEQ ID NO:53:

(i) SEQUENCE CHARACTERISTICS:
        (A) LENGTH: 15 amino acids
        (B) TYPE: amino acid
        (C) STRANDEDNESS:
        (D) TOPOLOGY: linear
```

(xi) SEQUENCE DESCRIPTION: SEQ ID NO:53:

Ala Glu Pro Lys Ser Ala Glu Pro Lys Pro Ala Glu Pro Lys Ser
1               5                   10                  15

(2) INFORMATION FOR SEQ ID NO:54:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:54:

Ala Glu Pro Lys Pro Ala Glu Pro Lys Ser Ala Glu Pro Lys Pro
1               5                   10                  15

(2) INFORMATION FOR SEQ ID NO:55:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:55:

Lys Ala Ala Ile Ala Pro Ala Lys Ala Ala Ala Ala Pro Ala Lys Ala
1               5                   10                  15

Ala Thr Ala Pro Ala
            20

(2) INFORMATION FOR SEQ ID NO:56:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:56:

Lys Ala Ala Ala Ala Pro Ala Lys Ala Ala Ala Ala Pro Ala Lys Ala
1               5                   10                  15

Ala Ala Ala Pro Ala
            20

(2) INFORMATION FOR SEQ ID NO:57:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:57:

Gly Asp Lys Pro Ser Pro Phe Gly Gln Ala Ala Ala Gly Asp Lys Pro
1               5                   10                  15

Ser Pro Phe Gly Gln Ala
            20

(2) INFORMATION FOR SEQ ID NO:58:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:58:

Lys Ala Ala Ala Ala Pro Ala Lys Ala Ala Ala Pro Ala Lys Ala
1               5                   10                  15

Ala Ala Ala Pro Ala
            20

(2) INFORMATION FOR SEQ ID NO:59:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:59:

Lys Ala Ala Thr Ala Pro Ala Lys Ala Ala Thr Ala Pro Ala Lys Ala
1               5                   10                  15

Ala Thr Ala Pro Ala
            20

(2) INFORMATION FOR SEQ ID NO:60:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:60:

Lys Ala Ala Ile Ala Pro Ala Lys Ala Ala Ile Ala Pro Ala Lys Ala
1               5                   10                  15

Ala Ile Ala Pro Ala
            20

(2) INFORMATION FOR SEQ ID NO:61:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:61:

Lys Ala Ala Ala Ala Pro Ala Lys Ala Ala Ala Ala Pro Ala
1               5                   10

(2) INFORMATION FOR SEQ ID NO:62:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:62:

Lys Ala Ala Ala Ala Pro Ala Lys Ala Ala Thr Ala Pro Ala
1               5                   10

(2) INFORMATION FOR SEQ ID NO:63:

(i) SEQUENCE CHARACTERISTICS:
        (A) LENGTH: 83 amino acids
        (B) TYPE: amino acid
        (C) STRANDEDNESS:
        (D) TOPOLOGY: linear (xi) SEQUENCE DESCRIPTION: SEQ ID NO:63:

Gly Asp Lys Pro Ser Pro Phe Gly Gln Ala Ala Gly Asp Lys Pro
1               5                   10                  15

Ser Pro Phe Gly Gln Ala Gly Cys Gly Ser Ser Met Pro Ser Gly Thr
            20                  25                  30

Ser Glu Glu Gly Ser Arg Gly Gly Ser Ser Met Pro Ala Gly Cys Gly
        35                  40                  45

Lys Ala Ala Ala Pro Ala Lys Ala Ala Ala Pro Ala Gly Cys
    50                  55                  60

Gly Ala Glu Pro Lys Ser Ala Glu Pro Lys Pro Ala Glu Pro Lys Ser
65              70                  75                  80

Gly Cys Gly (2) INFORMATION FOR SEQ ID NO:64:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:64:

Lys Thr Ala Ala Pro Pro Ala Lys Thr Ala Ala Pro Pro Ala Lys Thr
1               5                   10                  15

Ala Ala Pro Pro Ala
            20

(2) INFORMATION FOR SEQ ID NO:65:

(i) SEQUENCE CHARACTERISTICS:
        (A) LENGTH: 618 amino acids
        (B) TYPE: amino acid
        (C) STRANDEDNESS:
        (D) TOPOLOGY: linear (xi) SEQUENCE DESCRIPTION: SEQ ID NO:65:

Lys Ala Val Asp Pro Phe Gln Gly Thr Thr Pro Pro Tyr Lys Trp
1               5                   10                  15

Gln Glu Met Thr Gly Ser Glu Ala Ala Ala Gly Ser Leu Cys Val Pro
            20                  25                  30

Ser Leu Ala Glu Val Ala Gly Gly Val Phe Ala Val Ala Glu Ala Gln
            35                  40                  45

Arg Ser Glu Arg Asp Glu Ala Cys Gly His Ala Ala Ile Ala Thr Thr
    50                  55                  60

His Ile Glu Thr Gly Gly Gly Ser Lys Ala Ile Ser Ala Met Asp
65              70                  75                  80

Ala Gly Val Phe Leu Val Glu Leu Val Asp Ala Ala Ser Gly Thr Ile
            85                  90                  95

Arg Thr Arg Glu Lys Met Gln Pro Thr Thr Ile Val Ser Gly Asp Thr
            100                 105                 110

Ile Tyr Met Ala Leu Gly Asp Tyr Glu Lys Lys Thr Ser Gly Gly Arg
            115                 120                 125

Ala Ala Asp Ala Asp Gly Trp Arg Leu Leu Leu Met Arg Gly Thr Leu
    130                 135                 140

Thr Glu Asp Gly Gly Gln Lys Lys Ile Met Trp Gly Asp Ile Arg Ala
145             150                 155                 160

Val Asp Pro Val Ala Ile Gly Leu Thr Gln Phe Leu Lys Arg Val Ile
                165                 170                 175

```
Gly Gly Gly Gly Ser Gly Val Val Thr Lys Asn Gly Tyr Leu Val Leu
            180                 185                 190

Pro Met Gln Ala Val Glu Lys Asp Gly Arg Ser Val Val Leu Ser Met
            195                 200                 205

Arg Phe Asn Met Arg Ile Glu Ala Cys Glu Leu Ser Ser Gly Thr Thr
            210                 215                 220

Gly Ser Asn Cys Lys Glu Pro Ser Ile Ala Asn Leu Glu Gly Asn Leu
225                 230                 235                 240

Ile Leu Ile Thr Ser Cys Ala Ala Gly Tyr Tyr Glu Val Phe Arg Ser
            245                 250                 255

Leu Asp Ser Gly Thr Ser Trp Glu Met Ser Gly Arg Pro Ile Ser Arg
            260                 265                 270

Val Trp Gly Asn Ser Tyr Gly Arg Lys Gly Tyr Gly Val Arg Cys Gly
            275                 280                 285

Leu Thr Thr Val Thr Ile Glu Gly Arg Glu Val Leu Leu Val Thr Thr
            290                 295                 300

Pro Val Tyr Leu Glu Glu Lys Asn Gly Arg Gly Arg Leu His Leu Trp
305                 310                 315                 320

Val Thr Asp Gly Ala Arg Val His Asp Ala Gly Pro Ile Ser Asp Ala
            325                 330                 335

Ala Asp Asp Ala Ala Ser Ser Leu Leu Tyr Ser Ser Gly Gly Asn
            340                 345                 350

Leu Ile Ser Leu Tyr Glu Asn Lys Ser Glu Gly Ser Tyr Gly Leu Val
            355                 360                 365

Ala Val His Val Thr Thr Gln Leu Glu Arg Ile Lys Thr Val Leu Lys
            370                 375                 380

Arg Trp Gln Glu Leu Asp Glu Ala Leu Arg Thr Cys Arg Ser Thr Ala
385                 390                 395                 400

Thr Ile Asp Pro Val Arg Arg Gly Met Cys Ile Arg Pro Ile Leu Thr
            405                 410                 415

Asp Gly Leu Val Gly Tyr Leu Ser Gly Leu Ser Thr Gly Ser Glu Trp
            420                 425                 430

Met Asp Glu Tyr Leu Cys Val Asn Ala Thr Val His Gly Thr Val Arg
            435                 440                 445

Gly Phe Ser Asn Gly Val Thr Phe Glu Gly Pro Gly Ala Gly Ala Gly
            450                 455                 460

Trp Pro Val Ala Arg Ser Gly Gln Asn Gln Pro Tyr His Phe Leu His
465                 470                 475                 480

Lys Thr Phe Thr Leu Val Val Met Ala Val Ile His Asp Arg Pro Lys
            485                 490                 495

Lys Arg Thr Pro Ile Pro Leu Ile Arg Val Val Met Asp Asp Asn Asp
            500                 505                 510

Lys Thr Val Leu Phe Gly Val Phe Tyr Thr His Asp Gly Arg Trp Met
            515                 520                 525

Thr Val Ile His Ser Gly Gly Arg Gln Ile Leu Ser Thr Gly Trp Asp
            530                 535                 540

Pro Glu Lys Pro Cys Gln Val Leu Arg His Asp Thr Gly His Trp
545                 550                 555                 560

Asp Phe Tyr Val Asn Ala Arg Lys Ala Tyr Phe Gly Thr Tyr Lys Gly
            565                 570                 575

Leu Phe Ser Lys Gln Thr Val Phe His Thr Ser Asn Ser Thr Gly Arg
            580                 585                 590
```

```
Val Gly Lys Leu Gln Ser Pro Ala Ile Cys His Ser Ser Thr Pro Val
            595                 600                 605
Cys Ile Thr Glu Asp Ser Ile Pro Ser Ile
    610                 615
```

(2) INFORMATION FOR SEQ ID NO:66:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:66:

```
GGGGACAAAC CGTCTCCGTT CCAGGCTGCT GCTGGTGAC                              39
```

(2) INFORMATION FOR SEQ ID NO:67:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:67:

```
GAGACGGTTT GTCACCAGCA GCAGCCTGGA ACGGAGACGG TTTGTCCCC                   49
```

(2) INFORMATION FOR SEQ ID NO:68:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:68:

```
AAACCGTCTC CGTTCGGTCA GGCTGCTGAA CCGAAATCTG                             40
```

(2) INFORMATION FOR SEQ ID NO:69:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:69:

```
TTCGGTTCAG CAGATTTCGG TTCAGCAGCC TGACCGAACG                             40
```

(2) INFORMATION FOR SEQ ID NO:70:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:70:

CTGAACCGAA ACCGGCTGAA CCGAAAAGCG CTCTAGATGC ATGAATTCCA G          51

(2) INFORMATION FOR SEQ ID NO:71:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:71:

CTGGAATTCA TGCATCTAGA GCGCTTTTCG GTTCAGCCGG T                  41

(2) INFORMATION FOR SEQ ID NO:72:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:72:

AAAGCTGCTA TCGCTCCGGC TAAAGCTGCT GCTGCTCCGG CTAAAGCTG            49

(2) INFORMATION FOR SEQ ID NO:73:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trypanosoma cruzi (xi) SEQUENCE DESCRIPTION: SEQ ID NO:73:

CGGAGCAGCA GCAGCTTTAG CCGGAGCGAT AGCAGCTTT                     39

(2) INFORMATION FOR SEQ ID NO:74:

(i) SEQUENCE CHARACTERISTICS:
        (A) LENGTH: 29 base pairs
        (B) TYPE: nucleic acid
        (C) STRANDEDNESS: single
        (D) TOPOLOGY: linear

```
    (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:74:

CTACCGCTCC GGCCGGCTCG AGATGCATG                                    29

(2) INFORMATION FOR SEQ ID NO:75:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:75:

AATTCATGCA TCTCGAGCCG GCCGGAGCGG TAGCAGCTTT AGC                    43

(2) INFORMATION FOR SEQ ID NO:76:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:76:

TCTTCTATGC CGTCTGGTAC CTCTGAAGAA GGTTCTCGTG GTGGTTCTT              49

(2) INFORMATION FOR SEQ ID NO:77:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:77:

ACGAGAACCT TCTTCAGAGG TACCAGACGG CATAGAAGA                         39

(2) INFORMATION FOR SEQ ID NO:78:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:78:
```

```
CTATGCCGGC CGGCTCGAGA TGCATG                                                    26

(2) INFORMATION FOR SEQ ID NO:79:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:79:

AATTCATGCA TCTCGAGCCG GCCGGCATAG AAGAACCACC                                     40

(2) INFORMATION FOR SEQ ID NO:80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:80:

ATACCCCGGG GACAACCGTC TCC                                                       23

(2) INFORMATION FOR SEQ ID NO:81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Trypanosoma cruzi (xi) SEQUENCE DESCRIPTION: SEQ ID NO:81:

CGCCTTAGCC TGGAATTCAT GCATCT                                                    26
```

US 6,228,372 B1

COMPOUNDS AND METHODS FOR THE DETECTION AND PREVENTION OF T. CRUZI INFECTION

CROSS REFERENCE TO RELATED APPLICATIONS

This application is a continuation-in-part of U.S. application Ser. No. 08/834,306, filed Apr. 15, 1997, now U.S. Pat. No. 6,054,135, which claims priority from PCT Application No. PCT/US96/18624, filed Nov. 14, 1996.

TECHNICAL FIELD

The present invention relates generally to the diagnosis of T. cruzi infection. The invention is more particularly related to the use of one or more T. cruzi antigenic peptides, or antibodies thereto, in methods and diagnostic kits to screen individuals and blood supplies for T. cruzi infection. The invention is also directed to vaccine compositions for immunizing an individual to prevent Chagas' disease.

BACKGROUND OF THE INVENTION

Protozoan parasites are a serious health threat in many areas of the world. Trypanosoma cruzi (T. cruzi) is one such parasite that infects millions of individuals, primarily in Central and South America. Infections with this parasite can cause Chagas' disease, which may result in chronic heart disease and a variety of immune system disorders. It is estimated that 18 million people in Latin America are infected with T. cruzi, but there is no reliable treatment for the clinical manifestations of infection. No vaccine for the prevention of Chagas' disease is currently available.

The most significant route of transmission in areas where the disease is endemic is through contact with an infected triatomid bug. In other areas, however, blood transfusions are the dominant means of transmission. To inhibit the transmission of T. cruzi in such regions, it is necessary to develop accurate methods for diagnosing T. cruzi infection in individuals and for screening blood supplies. Blood bank screening is particularly important in South America, where 0.1%–62% of samples may be infected and where the parasite is frequently transmitted by blood transfusion. There is also increasing concern that the blood supply in certain U.S. cities may be contaminated with T. cruzi parasites.

The diagnosis of T. cruzi infection has been problematic, since accurate methods for detecting the parasite that are suitable for routine use have been unavailable. During the acute phase of infection, which may last for decades, the infection may remain quiescent and the host may be asymptomatic. As a result, serological tests for T. cruzi infection are the most reliable and the most commonly used.

Such diagnoses are complicated, however, by the complex life cycle of the parasite and the diverse immune responses of the host. The parasite passes through an epimastigote stage in the insect vector and two main stages in the mammalian host. One host stage is present in blood (the trypomastigote stage) and a second stage is intracellular (the amastigote stage). The multiple stages result in a diversity of antigens presented by the parasite during infection. In addition, immune responses to protozoan infection are complex, involving both humoral and cell-mediated responses to the array of parasite antigens.

While detecting antibodies against parasite antigens is the most common and reliable method of diagnosing clinical and subclinical infections, current tests are expensive and difficult. Most serological tests use whole or lysed T. cruzi and require positive results on two of three tests, including complement fixation, indirect immunofluorescence, passive agglutination or ELISA, to accurately detect T. cruzi infection. The cost and difficulty of such tests has prevented the screening of blood or sera in many endemic areas.

Accordingly, there is a need in the art for more specific and sensitive methods of detecting T. cruzi infections in blood supplies and individuals. The present invention fulfills these needs and further provides other related advantages.

SUMMARY OF THE INVENTION

Briefly stated, this invention provides compounds and methods for detecting and protecting against T. cruzi infection in individuals and in blood supplies, and for screening for T. cruzi infection in biological samples. In one aspect, the present invention provides methods for detecting T. cruzi infection in a biological sample, comprising (a) contacting the biological sample with a polypeptide comprising an epitope of a T. cruzi antigen having an amino acid sequence encoded by a nucleotide sequence recited in SEQ ID NO: 1–SEQ ID NO:22, or a variant of such an antigen that differs only in conservative substitutions and/or modifications; and (b) detecting in the biological sample the presence of antibodies that bind to the polypeptide, therefrom detecting T. cruzi infection in the biological sample.

In another aspect of this invention, polypeptides are provided comprising an epitope of a T. cruzi antigen having an amino acid sequence encoded by a nucleotide sequence recited in SEQ ID NO: 1–SEQ ID NO:21, or a variant of such an antigen that differs only in conservative substitutions and/or modifications.

Within related aspects, DNA sequences encoding the above polypeptides, expression vectors comprising these DNA sequences and host cells transformed or transfected with such expression vectors are also provided.

In another aspect, the present invention provides diagnostic kits for detecting T. cruzi infection in a biological sample, comprising (a) a polypeptide comprising an epitope of a T. cruzi antigen having an amino acid sequence encoded by a nucleotide sequence recited in SEQ ID NO: 1–SEQ ID NO:22, or a variant of such an antigen that differs only in conservative substitutions and/or modifications; and (b) a detection reagent.

In yet another aspect of the invention, methods for detecting the presence of T. cruzi infection in a biological sample are provided, comprising (a) contacting a biological sample with a monoclonal antibody that binds to an epitope of a T. cruzi antigen having an amino acid sequence encoded by a nucleotide sequence recited in SEQ ID NO :1–SEQ ID NO:22, or a variant of such an antigen that differs only in conservative substitutions and/or modifications; and (b) detecting in the biological sample the presence of T. cruzi parasites that bind to the monoclonal antibody.

Within related aspects, pharmaceutical compositions comprising the above polypeptides and a physiologically acceptable carrier, and vaccines comprising the above polypeptides in combination with an adjuvant, are also provided.

The present invention also provides, within other aspects, methods for inducing protective immunity against Chagas' disease in a patient, comprising administering to a patient a pharmaceutical composition or vaccine as described above.

Within other aspects, the present invention provides methods for detecting T. cruzi infection in a biological sample, comprising (a) contacting the biological sample with a first polypeptide comprising an epitope of a *T. cruzi* antigen having an amino acid sequence encoded by a nucleotide sequence recited in SEQ ID NO:1–SEQ ID NO:22, or a variant of said antigen that differs only in conservative substitutions and/or modifications; (b) contacting the biological sample with one or more additional polypeptides comprising one or more epitopes of other *T. cruzi* antigens, or a variant thereof that differs only in conservative substitutions and/or modifications; and (c) detecting in the biological sample the presence of antibodies that bind to one or more of said polypeptides, therefrom detecting *T. cruzi* infection in the biological sample. In one embodiment, the additional polypeptide comprises an epitope of TcD, or a variant thereof that differs only in conservative substitutions and/or modifications. In another embodiment, the additional polypeptides comprise an epitope of TcD (or a variant thereof that differs only in conservative substitutions and/or modifications) and an epitope of TcE (or a variant thereof that differs only in conservative substitutions and/or modifications). In yet another embodiment, the additional polypeptides comprise an epitope of TcD (or a variant thereof that differs only in conservative substitutions and/or modifications) and PEP-2 (or a variant thereof that differs only in conservative substitutions and/or modifications).

In yet further aspects, the present invention provides combination polypeptides comprising two or more polypeptides, each polypeptide comprising an epitope of a *T. cruzi* antigen having an amino acid sequence encoded by a nucleotide sequence recited in SEQ ID NO:1–SEQ ID NO:22, or a variant thereof that differs only in conservative substitutions and/or modifications. Combination polypeptides comprising at least one epitope of a *T. cruzi* antigen having an amino acid sequence encoded by a nucleotide sequence recited in SEQ ID NO:1–SEQ ID NO:22, or a variant thereof that differs only in conservative substitutions and/or modifications, and at least one epitope selected from the group consisting of TcD epitopes, TcE epitopes, PEP-2 epitopes and variants thereof that differ only in conservative substitutions and/or modifications are also provided. Such combination polypeptides may be prepared either by synthetic means or using recombinant DNA technology.

In related aspects, methods are provided for detecting *T. cruzi* infection in a biological sample, comprising (a) contacting the biological sample with at least one of the above combination polypeptides and (b) detecting in the biological sample the presence of antibodies that bind to the combination polypeptide.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
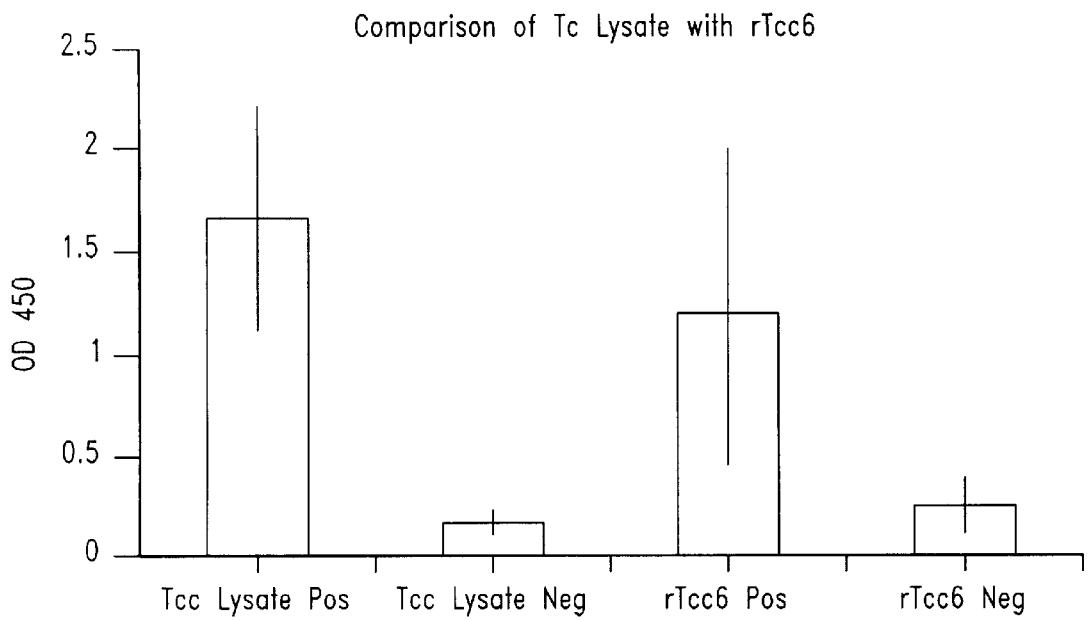
FIG. 1 is a graph comparing the reactivity of *T. cruzi* lysate and a representative polypeptide of the present invention (rTcc6) in an ELISA assay performed using sera from *T. cruzi*-infected (Pos) and uninfected (Neg) individuals. The bars represent ±1 standard deviation.

As noted above, the present invention is generally directed to compounds and methods for detecting and protecting against *T. cruzi* infection in individuals and in blood supplies. The compounds of this invention generally comprise one or more epitopes of *T. cruzi* antigens. In particular, polypeptides comprising an epitope of a *T. cruzi* antigen having an amino acid sequence encoded by a nucleotide sequence recited in SEQ ID NO:1–SEQ ID NO:22are preferred. As used herein, the term "polypeptide" encompasses amino acid chains of any length, including full length (i.e., native) antigens. Thus, a polypeptide comprising an epitope may consist entirely of the epitope or may contain additional sequences. The additional sequences may be derived from the native antigen or may be heterologous, and such sequences may (but need not) be antigenic. A protein "having" a particular amino acid sequence is a protein that contains, within its full length sequence, the recited sequence. Such a protein may, or may not, contain additional amino acid sequence. The use of one or more epitopes from additional *T. cruzi* proteins, prior to or in combination with one or more epitopes of sequences recited herein, to enhance the sensitivity and specificity of the diagnosis, is also contemplated.

An "epitope," as used herein, is a portion of a *T. cruzi* antigen that reacts with sera from *T. cruzi*-infected individuals (i.e., an epitope is specifically bound by one or more antibodies within such sera). Epitopes of the antigens described in the present application may generally be identified using methods known to those of ordinary skill in the art, such as those summarized in Paul, *Fundamental Immunology*, 3rd ed., 243–247 (Raven Press, 1993) and references cited therein. For example, a polypeptide derived from a native *T. cruzi* antigen may be screened for the ability to react with pooled sera obtained from *T. cruzi*-infected patients. Suitable assays for evaluating reactivity with *T. cruzi*-infected sera, such as an enzyme linked immunosorbent assay (ELISA), are described in more detail below, and in Harlow and Lane, *Antibodies: A Laboratory Manual*, Cold Spring Harbor Laboratory, 1988. An epitope of a polypeptide is a portion that reacts with such antisera at a level that is substantially similar to the reactivity of the full length polypeptide. In other words, an epitope may generate at least about 80%, and preferably at least about 100%, of the response generated by the full length polypeptide in an antibody binding assay (e.g., an ELISA).

The compounds and methods of this invention also encompass variants of the above polypeptides. As used herein, a "variant" is a polypeptide that differs from the recited polypeptide only in conservative substitutions or modifications, such that it retains the antigenic properties of the recited polypeptide. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other conservative modifications, including the deletion or addition of amino acids that have minimal influence on the antigenic properties, secondary structure and hydropathic nature of the polypeptide. For example, the polypeptide may be conjugated to a linker or other sequence for ease of synthesis or to enhance binding of the polypeptide to a solid support.

In a related aspect, combination polypeptides comprising epitopes of multiple *T. cruzi* antigens are disclosed. A "combination polypeptide" is a polypeptide in which epitopes of different *T. cruzi* antigens, or variants thereof, are joined, for example through a peptide linkage, into a single amino acid chain. The amino acid chain thus formed may be either linear or branched. The epitopes may be joined directly (i.e., with no intervening amino acids) or may be joined by way of a linker sequence (e.g., Gly-Cys-Gly) that does not significantly alter the antigenic properties of the epitopes. The peptide epitopes may also be linked through non-peptide linkages, such as hetero- or homo-bifunctional agents that chemically or photochemically couple between specific functional groups on the peptide epitopes such as through amino, carboxyl, or sulfhydryl groups. Bifunctional agents which may be usefully employed in the combination polypeptides of the present invention are well known to those of skill in the art. Epitopes may also be linked by means of a complementary ligand/anti-ligand pair, such as avidin/biotin, with one or more epitopes being linked to a first member of the ligand/anti-ligand pair and then being bound to the complementary member of the ligand/anti-ligand pair either in solution or in solid phase. A combination polypeptide may contain multiple epitopes of polypeptides as described herein and/or may contain epitopes of one or more other *T. cruzi* antigens, such as TcD, TcE or PEP-2, linked to an epitope described herein.

In general, *T. cruzi* antigens, and DNA sequences encoding such antigens, may be prepared using any of a variety of procedures. For example, a *T. cruzi* cDNA or genomic DNA expression library may be screened with pools of sera from *T. cruzi*-infected individuals. Such screens may generally be performed using techniques well known to those of ordinary skill in the art, such as those described in Sambrook et al., *Molecular Cloning: A Laboratory Manual,* Cold Spring Harbor Laboratories, Cold Spring Harbor, N.Y., 1989. Briefly, the bacteriophage library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents for screening purposes contain a "binding agent," such as Protein A, Protein G, IgG or a lectin, coupled to a reporter group. Preferred reporter groups include, but are not limited to, enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing cDNAs that express a protein that binds to an antibody in the serum may be isolated and purified by techniques known to those of ordinary skill in the art. Appropriate methods may be found, for example, in Sambrook et al., *Molecular Cloning: A Laboratory Manual,* Cold Spring Harbor Laboratories, Cold Spring Harbor, N.Y., 1989.

DNA molecules having the nucleotide sequences recited in SEQ ID NO:1–SEQ ID NO:18 may be isolated by screening a *T. cruzi* genomic expression library with pools of sera from *T. cruzi*-infected individuals, as described above. More specifically, DNA molecules having the nucleotide sequences recited in SEQ ID NO: 1–SEQ ID NO:16 may be isolated by screening the library with a pool of sera that displays serological reactivity (in an ELISA or Western assay) with parasite lysate and/or one or both of the *T. cruzi* antigens TcD and TcE, described in U.S. Pat. No. 5,304,371 and U.S. Ser. No. 08/403,379, filed Mar. 14, 1995. A subsequent screen is then performed with patient sera lacking detectable anti-TcD antibody. A DNA molecule having the nucleotide sequences recited in SEQ ID NO:17 (5' end) and SEQ ID NO:18 (3' end) may be isolated by screening the genomic expression library with a pool of sera that displays lower serological reactivity (i.e., detects a signal less than 3 standard deviations over background reactivity in an ELISA or Western assay) with lysate, TcD and TcE, followed by a subsequent screen with patient sera lacking detectable anti-TcD antibody.

DNA molecules having the sequences recited in SEQ ID NO:19–SEQ ID NO:22 may be obtained by screening an unamplified *T. cruzi* cDNA expression library with sera (both higher and lower serological reactivity) from *T. cruzi*-infected individuals, as described above.

Alternatively, DNA molecules having the sequences recited in SEQ ID NO:1–SEQ ID NO:22 may be amplified from *T. cruzi* genomic DNA or cDNA via polymerase chain reaction. For this approach, sequence-specific primers may be designed based on the sequences provided in SEQ ID NO:1–SEQ ID NO:22, and may be purchased or synthesized. An amplified portion of the DNA sequences may then be used to isolate the full length genomic or cDNA clones using well known techniques, such as those described in Sambrook et al., *Molecular Cloning: A Laboratory Manual*, Cold Spring Harbor Laboratories, Cold Spring Harbor, N.Y. (1989).

Epitopes of antigens having amino acid sequences encoded by the above DNA sequences may generally be identified by generating polypeptides containing portions of the native antigen and evaluating the reactivity of the polypeptides with sera from *T. cruzi*-infected individuals, as described above. In many instances, peptides comprising one or more repeat sequences found in the native antigen contain an epitope. Such repeat sequences may be identified based on inspection of the above nucleotide sequences. Representative repeat sequences for antigens encoded by the above DNA sequences are provided in SEQ ID NO:23–SEQ ID NO:36 and SEQ ID NO:47–SEQ ID NO:49. More specifically, repeat sequences for the sequence recited in SEQ ID NO:3 are provided in SEQ ID NO:23 (Frame 1), SEQ ID NO:24 (Frame 2) and SEQ ID NO:25 (Frame 3). Repeat sequences for the sequence recited in SEQ ID NO:4 are provided in SEQ ID NO:26 (Frame 1) and SEQ ID NO:27 (Frame 3) and repeat sequences for SEQ ID NO:9 are provided in SEQ ID NO:47 (Frame 1), SEQ ID NO:48 (Frame 2) and SEQ ID NO:49 (Frame 3). For SEQ ID NO:12, repeat sequences are provided in SEQ ID NO:28 (Frame 1), SEQ ID NO:29 (Frame 2) and SEQ ID NO:30 (Frame 3). SEQ ID NO:31 recites a repeat sequence for SEQ ID NO:15. For SEQ ID NO:16, repeat sequences are provided in SEQ ID NO:32 (Frame 2) and SEQ ID NO:33 (Frame 3). Finally, repeat sequences for SEQ ID NO:18 are provided in SEQ ID NO:34 (Frame 1), SEQ ID NO:35 (Frame 2) and SEQ ID NO:36 (Frame 3).

The polypeptides described herein may be generated using techniques well known to those of ordinary skill in the art. Polypeptides having fewer than about 100 amino acids, and generally fewer than about 50 amino acids, can be synthesized using, for example, the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied Biosystems Division, Foster City, Calif. Thus, for example, polypeptides comprising the above repeat sequences or portions thereof, may be synthesized by this method. Similarly, epitopes of other native antigens, or variants thereof, may be prepared using an automated synthesizer.

Alternatively, the polypeptides of this invention may be prepared by expression of recombinant DNA encoding the polypeptide in cultured host cells. Preferably, the host cells are *E. coli*, yeast, an insect cell line (such as Spodoptera or Trichoplusia) or a mammalian cell line, including (but not limited to) CHO, COS and NS-1. The DNA sequences expressed in this manner may encode naturally occurring proteins, such as full length antigens having the amino acid sequences encoded by the DNA sequences of SEQ ID NO:1–SEQ ID NO:22, portions of naturally occurring proteins, or variants of such proteins. Representative polypeptides encoded by such DNA sequences are provided in SEQ ID NO:37–SEQ ID NO:46, SEQ ID NO:52, and SEQ ID NO:65.

Expressed polypeptides of this invention are generally isolated in substantially pure form. Preferably, the polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

In another aspect of this invention, methods for detecting *T. cruzi* infection in individuals and blood supplies are disclosed. In one embodiment, *T. cruzi* infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, *T. cruzi* infection may be detected using any one or more of the polypeptides described above, or variants thereof, to determine the presence or absence of antibodies to the polypeptide or polypeptides in the sample, relative to a predetermined cut-off value.

There are a variety of assay formats known to those of ordinary skill in the art for using purified antigen to detect antibodies in a sample. See, e.g., Harlow and Lane, *Antibodies: A Laboratory Manual*, Cold Spring Harbor Laboratory, 1988. In a preferred embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen. Nitrocellulose will bind approximately 100 µg of protein per $cm^3$.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20 TM (Sigma Chemical Co., St. Louis, Mo.). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detect the presence of *T. cruzi* antibody within a *T. cruzi*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *T. cruzi* antibodies in the sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *T. cruzi* antibodies and *T. cruzi* infection. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (ie., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *T. cruzi* infection.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of *T. cruzi* antibodies in the sample. Such tests can typically be performed with a very small amount (e.g., one drop) of patient serum or blood.

The assays discussed above may be performed using one or more of the polypeptides described herein. Alternatively, the sensitivity may be improved by using epitopes of one or more additional *T. cruzi* antigens in combination with the above polypeptide(s). In particular, epitopes of TcD (disclosed, for example, in U.S. Pat. No. 5,304,371), PEP-2 and/or TcE (both of which are disclosed, for example, in U.S. Ser. No. 08/403,379, filed Mar. 14, 1995) may be used in conjunction with the above polypeptide(s). The PEP-2 antigenic epitope is also discussed in Peralta et al., *J. Clin. Microbiol.* 32:971–74, 1994. The sequence of TcD is provided in SEQ ID NO:50, the sequence of TcE is provided in SEQ ID NO:51. The TcD antigenic epitope preferably has the amino acid sequence Ala Glu Pro Lys Ser Ala Glu Pro Lys Pro Ala Glu Pro Lys Ser (SEQ ID NO:53)or the amino acid sequence Ala Glu Pro Lys Pro Ala Glu Pro Lys Ser Ala Glu Pro Lys Pro (SEQ ID NO:54). The TcE epitope preferably has the amino acid sequence Lys Ala Ala Ile Ala Pro Ala Lys Ala Ala Ala Pro Ala Lys Ala Ala Thr Ala Pro Ala (SEQ ID NO: 55) or the amino acid sequence Lys Ala Ala Ala Ala Pro Ala Lys Ala Ala Ala Ala Pro Ala Lys Ala Ala Ala Ala Pro Ala (SEQ ID NO:56), and the PEP2 epitope preferably has the amino acid sequence Gly Asp Lys Pro Ser Pro Phe Gly Gln Ala Ala Ala Gly Asp Lys Pro Ser Pro Phe Gly Gln Ala (SEQ ID NO:57).

Additional epitopes may be present within the same polypeptide (i.e., in a combination polypeptide) or may be included in separate polypeptides. Combination polypeptides may be prepared either synthetically, as described below in Example 2, or using recombinant DNA technology as detailed below in Example 7. Preferably, the polypeptides are immobilized by adsorption on a solid support such as a well of a microtiter plate or a membrane, as described above, such that a roughly similar amount of each polypeptide contacts the support, and such that the total amount of polypeptide in contact with the support ranges from about 1 ng to about 10 µg. The remainder of the steps may generally be performed as described above.

The polypeptides described above may also be used following diagnosis using one or more of the epitopes from TcD, TcE and/or PEP2. In this embodiment, the polypeptides of the present invention are used to confirm a diagnosis of *T. cruzi* infection based on a screen with TcD, TcE and/or PEP2. Diagnosis of *T. cruzi* infection using epitopes from TcD, TcE and/or PEP2 is described in U.S. Ser. No. 08/403,379, filed Mar. 14, 1995.

In yet another aspect of this invention, methods are provided for detecting *T. cruzi* in a biological sample using monospecific antibodies (which may be polyclonal or monoclonal) to one or more epitopes, as described above. Antibodies to purified or synthesized polypeptides may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (ie., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Monospecific antibodies to epitopes of one or more of the polypeptides described herein may be used to detect *T. cruzi* infection in a biological sample using any of a variety of immunoassays, which may be direct or competitive. Suitable biological samples for use in this aspect of the present invention are as described above. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of *T. cruzi* in the sample. To determine the presence or absence of *T. cruzi* infection, the signal detected from the reporter group that remains bound to the solid support is generally compared to a signal that corresponds to a predetermined cut-off value. Such cut-off values may generally be determined as described above. Any of the reporter groups discussed above in the context of ELISAs may be used to label the monospecific antibodies, and binding may be detected by any of a variety of techniques appropriate for the reporter group employed. Other formats for using monospecific antibodies to detect *T. cruzi* in a sample will be apparent to those of ordinary skill in the art, and the above formats is provided solely for exemplary purposes.

In another aspect of this invention, vaccines and pharmaceutical compositions are provided for the prevention of *T. cruzi* infection, and complications thereof, in a mammal. The pharmaceutical compositions generally comprise one or more polypeptides, containing one or more epitopes of *T. cruzi* proteins, and a physiologically acceptable carrier. The vaccines comprise one or more of the above polypeptides and an adjuvant, for enhancement of the immune response.

Routes and frequency of administration and polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2–6 week period. Preferably, two doses are administered, with the second dose 2–4 weeks later than the first. A suitable dose is an amount of polypeptide that is effective to raise antibodies in a treated mammal that are sufficient to protect the mammal from *T. cruzi* infection for a period of time. In general, the amount of polypeptide present in a dose ranges from about 1 µg to about 100 mg per kg of host, typically from about 10 µg to about 1 mg, and preferably from about 100 µg to about 1 µg. Suitable dose sizes will vary with the size of the animal, but will typically range from about 0.01 mL to about 5 mL for 10–60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The following Examples are offered by way of illustration and not by way of limitation.

EXAMPLES

Example 1

Preparation of DNA Encoding *T. cruzi* Antigens

This Example illustrates the preparation of genomic and cDNA molecules encoding *T. cruzi* Antigens.

A. Preparation of Genomic Clones

A genomic expression library was constructed from randomly sheared *T. cruzi* genomic DNA (Tulahuen C2 strain) using the Lambda ZAP expression system (Stratagene, La Jolla, Calif.) according to the manufacturer's instructions. In one screen, the library was screened with a pool of sera from five patients that displayed high reactivity with parasite lysate and/or one or both of the *T. cruzi* antigens TcD and TcE, described in U.S. Pat. No. 5,304,371 and U.S. Ser. No. 08/403,379, filed Mar. 14, 1995. Each of the five patients' sera was determined to be reactive based on Western and ELISA assays with whole lysate and/or TcD or TcE. Anti-*E. coli* reactivity was removed from the serum prior to screening by adsorption. 50,000 pfu of the unamplified library was screened with the serum pool and plaques expressing proteins that reacted with the serum were detected using protein A-horseradish peroxidase (with the ABTS substrate). A subsequent screen was then performed with a pool of sera from three patients lacking detectable anti-TcD antibody in Western and ELISA assays using recombinant TcD.

A similar screen was performed using a pool of sera that displayed low reactivity with lysate, TcD and TcE (ie., detected a signal less than 3 standard deviations over background reactivity in an ELISA or Western assay), followed by a subsequent screen with patient sera lacking detectable anti-TcD antibody, as described above.

Twenty-eight clones that expressed proteins which reacted with both pools of sera in at least one of the above screens were then isolated. Excision of the pBSK(–) phagemid (Stratagene, Inc., La Jolla, Calif.) was carried out according to the manufacturer's protocol. Overlapping clones were generated by exonuclease III digestion and single-stranded templates were isolated after infection with VCSM 13 helper phage. The DNA was sequenced by the dideoxy chain termination method or by the Taq di-terminator system, using an Applied Biosystem automated sequencer, Model 373A.

Of the 28 clones, five had been reported previously, two were identical, and eight contained identical peptide sequences represented by a degenerate 42 base pair repeat. SEQ ID NO:16 shows the prototype clone containing the 42 base pair repeat sequence. Accordingly, 14 novel DNA sequences encoding *T. cruzi* antigens were prepared using the above screen with the reactive pool of sera (shown in SEQ ID NO:1–SEQ ID NO:16, where SEQ ID NO:4 and SEQ ID NO:5 represent the 5' and 3' ends, respectively, of a single clone, SEQ ID NO:9 and SEQ ID NO:10 represent the 5' and 3' ends, respectively, of a single clone. One novel sequence was obtained with the screen employing the sera with low reactivity (shown in SEQ ID NO:17 (5' end) and SEQ ID NO:18 (3' end)).

B. Preparation of cDNA Clones

Poly A+ RNA was purified from the intracellular amastigote stage of *T. cruzi* (Tulahuen C2 strain). The RNA was reverse transcribed and used in the construction of a unidirectional cDNA expression library in the Lambda UniZap expression vector (Stratagene, La Jolla, Calif.) according to the manufacturer's instructions. 50,000 pfu of the unamplified library was screened with a serum pool containing patient sera that displayed both high and low serological reactivity, followed by a subsequent screen with patient sera lacking detectable anti-TcD antibody, as described above. A total of 32 clones were isolated from this screen. Twenty-five of these clones were proteins of the translational apparatus that have been previously identified as highly immunogenic, and all were different from the clones identified by screening the genomic expression library. The remaining seven are represented by the sequences provided in SEQ ID NO:19–SEQ ID NO:22. The sequence recited in SEQ ID NO:22 is that of *T. cruzi* ubiquitin.

Example 2

Synthesis of Synthetic Polypeptides

This Example illustrates the synthesis of polypeptides having sequences derived from *T. cruzi* antigens described herein.

Polypeptides may be synthesized on a Millipore 9050 peptide synthesizer using FMOC chemistry with HBTU (O-benzotriazole-N,N,N',N'-tetramethyuronium hexafluorophosphate) activation. A gly-cys-gly sequence may be attached to the amino or carboxyl terminus of the peptide to provide a method of conjugation or labeling of the peptide. Cleavage of the peptides from the solid support may be carried out using the following cleavage mixture: trifluoroacetic acid:ethanediol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1%TFA) may be used to elute the peptides. Following lyophilization of the pure fractions, the peptides are characterized using electrospray mass spectrometry and by amino acid analysis.

This procedure was used to synthesize peptides such as Tcc22-1, Tcc22-1+, Tcc22-2.1 (contained within SEQ ID NO:41), TcLo1.1,1.2 and 1.3 (contained within SEQ ID NOs 34, 35 and 36) and TcHi10.1 and 10.3 (SEQ ID NOs 26 and 27) which have the following sequences:

```
Tcc22-1       VRASNCRKKACGHCSNLRMKKK

Tcc22-1+      EALAKKYNWEKKVCRRCYARLPVRASNCRKKACGHCSNLRMKKK

Tcc22-2.1     VLRLRGGVMEPTLEALAKKYNWEKKVCRRCYARL

TcLo1.1       GYVRGRKQRWQLHACGYVRGRKQRRQLHACGYVRGRKQRWQLHAF

TcLo1.2       GTSEEGSRGGSSMPSGTSEBGSRGGSSMPA

TcLo1.3       VRPRKEAEVAAPCLRVRPRKEAEEAAPCLR

TcHi10.1      SVPGKRLRNSHGKSLRNVHGKRPKNEHGKRLRSVPNERLR

TcHi10.3      EAEELARQESEERARQEAEERAWQEAEERAQREAEERAQR
```

Example 3

Serological Reactivity of *T. cruzi* Recombinant Antigens

This example illustrates the diagnostic properties of several recombinant antigens found to be serologically active. This includes studies of reactivity with *T. cruzi* positive and negative sera as well as cross reactivity studies with sera from patients with other diseases.

Assays were performed in 96 well plates (Corning Easiwash, Corning, N.Y.). Wells were coated in 50 μl of carbonate coating buffer pH 9.6. For *T. cruzi* lysate, 100 ng/well was used, and for each of the recombinant antigens 200 ng/well was used. The wells were coated overnight at 4° C. (or 2 hours at 37° C.). The plate contents were then removed and wells were blocked for 2 hours with 200 μl of PBS/1%BSA. After the blocking step, the wells were washed five times with PBS/0.1% Tween 20™. 50 μl of sera (either positive or negative for *T. cruzi* infection), diluted 1:50 in PBS/0.1% Tween 20/0.1%BSA was then added to each well and incubated for 30 minutes at room temperature. The plates were then washed again five times with PBS/ 0.1% Tween 20™.

The enzyme conjugate (horse radish peroxidase-Protein A, Zymed, San Francisco, Calif.) was then diluted 1:20,000 in PBS/0.1% Tween 20™/0.1%BSA, and 50 μl of the diluted conjugate was added to each well and incubated for 30 minutes at room temperature. Following incubation the wells were again washed five times with PBS/0.1% Tween 20™. 100 μl of the peroxidase substrate, tetramethylbenzidine (Kirkegaard and Perry Laboratories, Gaithersburg, Md.) was added, undiluted, to each of the wells and incubated for 15 minutes. The reaction was stopped by the addition of 100 μl of 1N $H_2SO_4$ to each well, and the plates were read at 450 nm.

Figure 2:
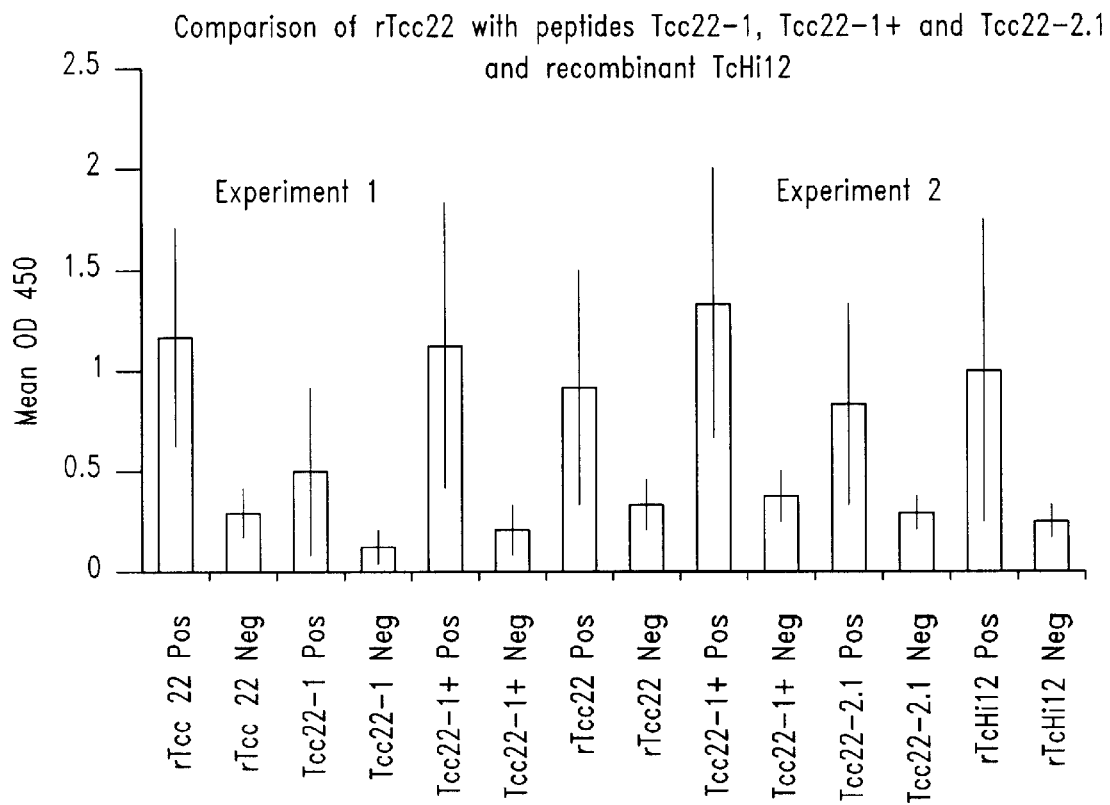
FIG. 2 is a graph presenting a comparison of the reactivity of representative polypeptides of the subject invention in an ELISA assay performed using sera from *T. cruzi*-infected (Pos) and uninfected (Neg) individuals. Experiment 1 shows a comparison of rTcc22 and the peptides Tcc22-1 and Tcc22-1+; Experiment 2 shows a comparison of rTcc22, rTcHi12 and the peptides Tcc22-1, Tcc22-1+ and cc22-2.1. The bars represent ±1 standard deviation.
Figure 3:
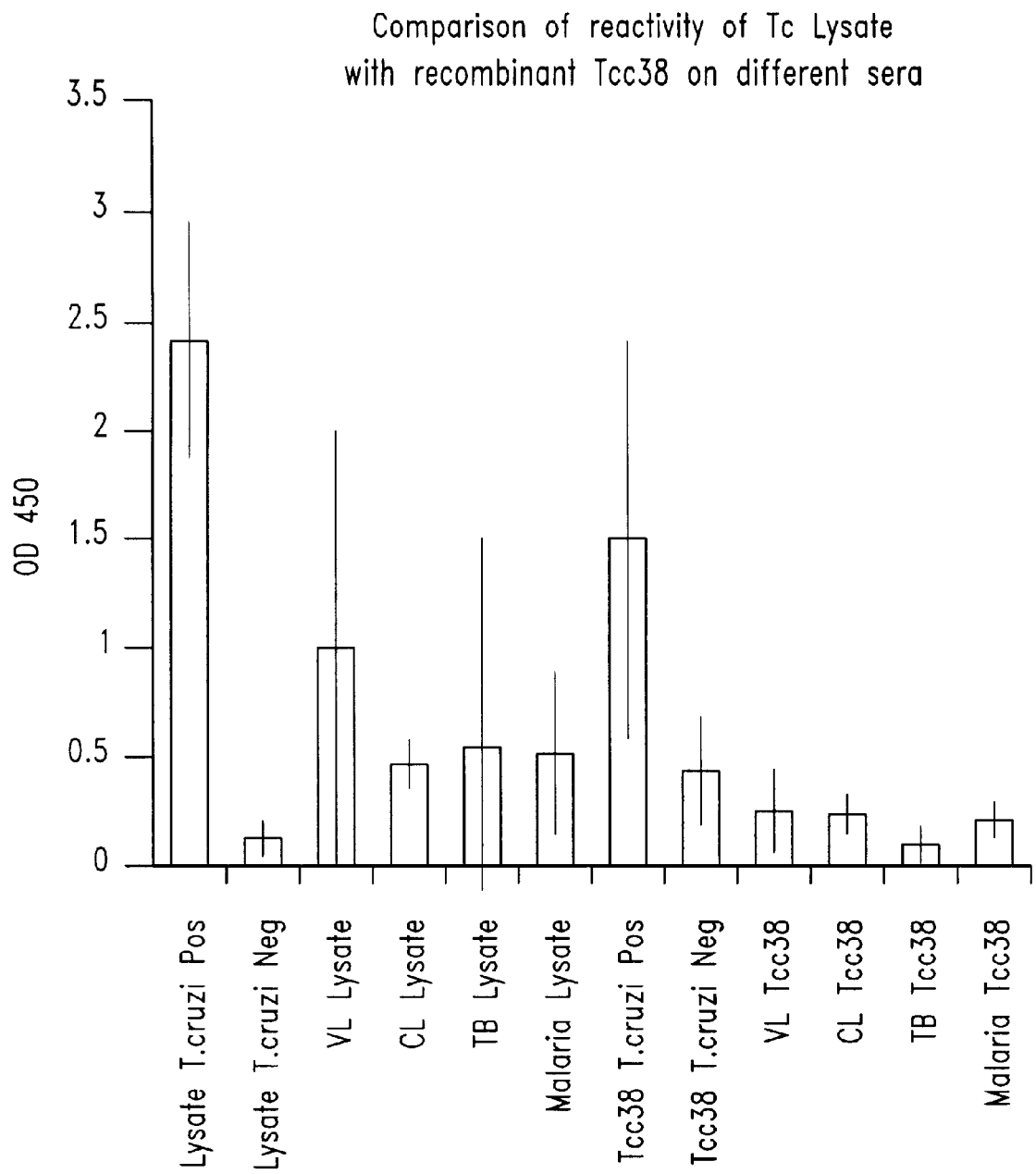
FIG. 3 is a graph depicting a comparison of the reactivity of *T. cruzi* lysate and a representative polypeptide (Tcc38) in an ELISA assay performed using sera from *T. cruzi*-infected (Pos) and uninfected (Neg) individuals, as well as using sera from individuals with visceral leishmaniasis (VL), cutaneous leishmaniasis (CL), tuberculosis (TB) and malaria. The bars represent ±1 standard deviation.

FIG. 1 shows the reactivity of the recombinant rTcc6 (SEQ ID NO:39) as compared to that of *T. cruzi* lysate. Based on a cutoff of the mean of the negatives plus 3 standard deviations, 49 out of 50 serum samples were positive with lysate, and 34 out of 50 were positive with rTcc6. In a similar study (shown in FIG. 2), the recombinant rTcc22 (SEQ ID NO:41) was found to have a sensitivity of 79.2% (38 out of 48 serum samples were positive). Comparative studies of the recombinant rTcc38 (SEQ ID NO:38) with *T. cruzi* lysate using similar criteria showed that 24/39 were positive compared with 39/39 for lysate (FIG. 3). Tcc38 when tested with potentially cross reacting sera showed improved specificity over *T. cruzi* lysate.

The recombinant TcHi12 (SEQ ID NO:37) was also found to be immunoreactive (FIG. 2) having a sensitivity of 62.5% (15/24).

Example 4

Serological Reactivity of *T. cruzi* Synthetic Peptide Antigens

This example illustrates the diagnostic properties of several of the peptides described in Example 2. These peptides were tested for reactivity with *T. cruzi* positive and negative sera and, in some cases, for cross reactivity with sera from patients with other, potentially cross reactive, diseases.

Figure 4:
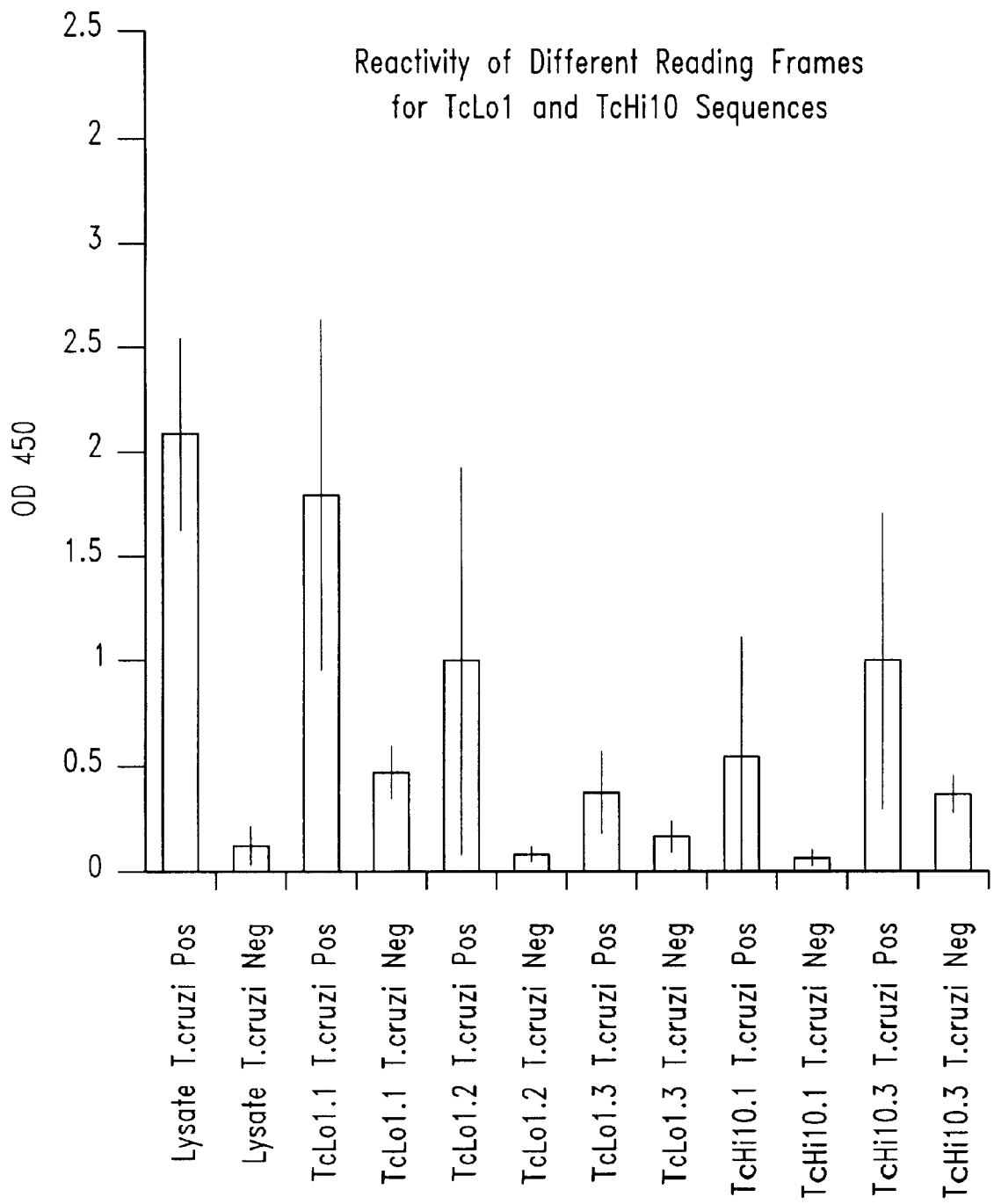
FIG. 4 is a graph presenting a comparison of the reactivity of *T. cruzi* lysate and several polypeptides of the present invention, representing different reading frames of the TcLo1 and TcHi10 antigens, in an ELISA assay performed using sera from *T. cruzi*-infected (Pos) and uninfected (Neg) individuals. The bars represent +1 standard deviation.
Figure 5:
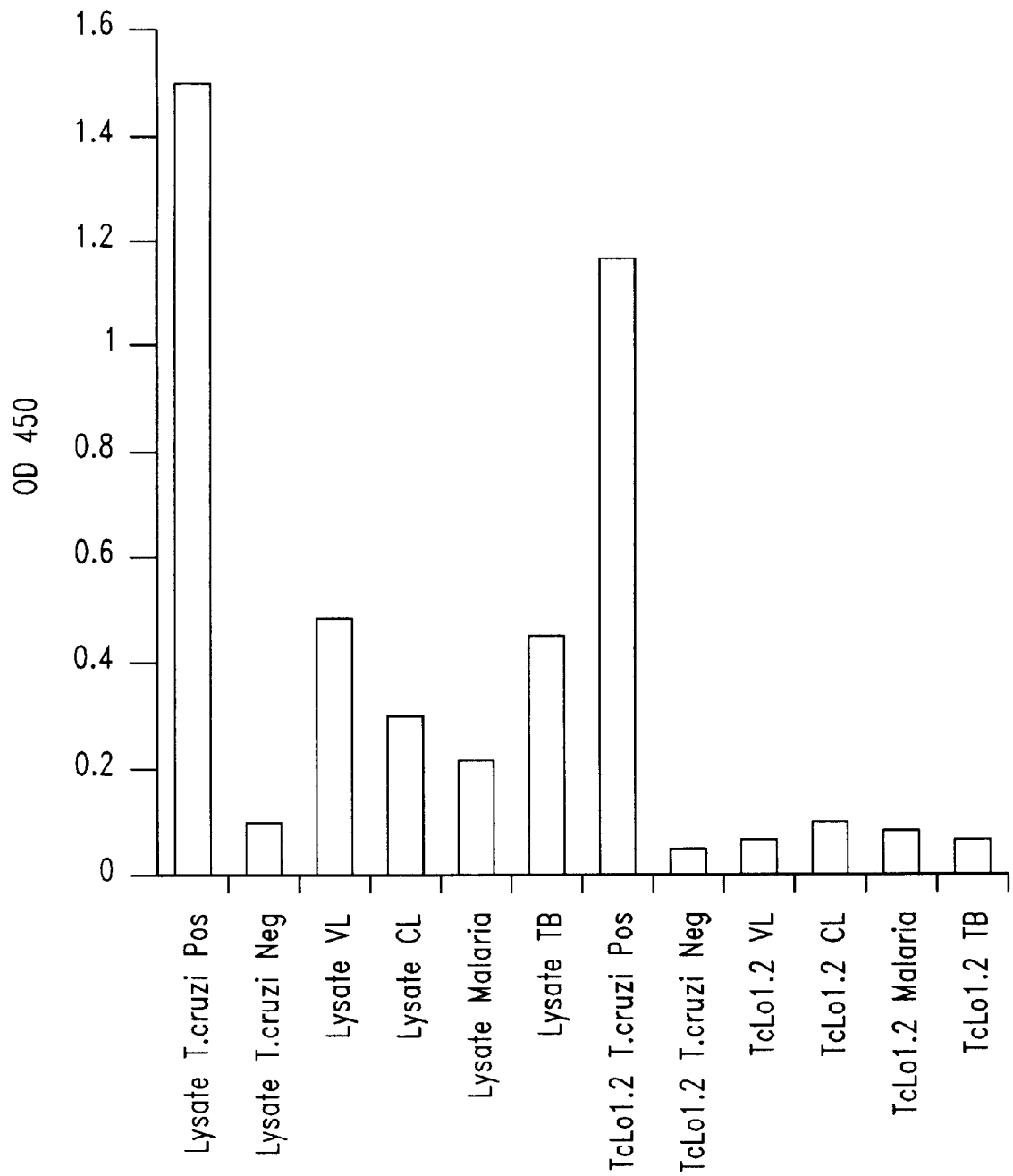
FIG. 5 is a graph comparing the reactivity of *T. cruzi* lysate and a representative polypeptide (TccLo1.2) in an ELISA assay performed using sera from *T. cruzi*-infected (Pos) and uninfected (Neg) individuals, as well as sera from individuals with visceral leishmaniasis (VL), cutaneous leishmaniasis (CL), malaria and tuberculosis (TB).

The first group of peptides included different reading frames to determine the most reactive repeat sequence. The peptides tested were TcLo1.1 (contained within SEQ ID NO:34), TcLo1.2 (contained within SEQ ID NO:35) and TcLo1.3 (contained within SEQ ID NO:36), representing reading frames 1, 2 and 3 of the DNA sequence provided in SEQ ID NO:18, and TcHi10.1 (SEQ ID NO:26) and TcHi10.3 (SEQ ID NO:27) which represent two of the reading frames for the TcHi10 sequence (shown in SEQ ID NO:5). The data is shown in FIG. 4. In the case of the TcLo frames, both the TcLo1.1 and 1.2 peptides were strongly reactive but the TcLo1.2 was superior in signal to noise when tested on sera from *T. cruzi* positive and negative individuals. TcLo1.3 had lower signal but also low background. In this study lysate detected 24/24 positives, TcLo1.1 detected 21/24, TcLo1.2 detected 23/24 and TcLo1.3 detected 15/24. In the same study, the two frames TcHi10.1 and 10.3 detected 19/24 and 14/24 positives respectively, but with lower signal than for TcLo1. Cross reactivity studies with these different reading frames demonstrate that TcLo1.2 has minimal cross reactivity with the sera tested (FIG. 5) as compared to *T. cruzi* lysate.

As discussed in Example 2, overlapping peptides were also synthesized for rTcc22 to determine the active epitope. The peptides Tcc22- 1, 1+ and 2 were tested with *T. cruzi* positive and negative sera. The results are shown in FIG. 2. The Tcc22-1+ and Tcc22-2.1 peptides were more reactive than the Tcc22-1 peptide. In the first experiment, Tcc22-1 and Tcc22-1+ detected 29/48 and 36/48 positives as compared to the recombinant Tcc22 which detected 38/48 positives. In a subsequent experiment, Tcc22-2.1 was also shown to be reactive but with less signal than Tcc22-1+ at the same plate coating level.

A polypeptide having the TcHi15 frame 3 repeat sequence (SEQ ID NO:49) was also synthesized and tested in an ELISA assay using a coating level of 200 ng/well. A total of 48 *T. cruzi* positive sera and 26 negative sera were tested in order to determine the reactivity of this peptide sequence. In this study, the peptide had a sensitivity of 68.75% (detecting 33 out of 48 positives) and a specificity of 92.3% (24 out of 36 negatives), indicating that this polypeptide has potential significance in detecting *T. cruzi* infections. The results of this assay are presented in Table 1, below.

TABLE 1

Reactivity of TcHi15 Frame 3 Polypeptide with *T. cruzi*-Positive and Negative Sera

| Sample ID | T. cruzi Status | OD 450 | Sample ID | T. cruzi Status | OD 450 |
|---|---|---|---|---|---|
| Tc011095-1 | Positive | 0.696 | DL4-0106 | Negative | 0.167 |
| Tc011095-2 | Positive | 0.699 | DL4-0112 | Negative | 0.05 |
| Tc011095-3 | Positive | 1.991 | DL4-0127 | Negative | 0.240 |
| Tc011095-4 | Positive | 3 | DL4-0140 | Negative | 0.008 |
| Tc011095-5 | Positive | 0.098 | DL4-0145 | Negative | 0.107 |
| Tc011095-6 | Positive | 0.238 | DL4-0161 | Negative | 0.119 |
| Tc011095-7 | Positive | 0.115 | DL4-0162 | Negative | 1.187 |
| Tc011095-8 | Positive | 0.156 | DL4-0166 | Negative | 0.210 |
| Tc011095-9 | Positive | 0.757 | DL4-0167 | Negative | 0.131 |
| Tc011095-10 | Positive | 1.147 | DL4-0172 | Negative | 0.073 |
| Tc011095-11 | Positive | 0.264 | DL4-0175 | Negative | 0.117 |
| Tc011095-12 | Positive | 1.7 | DL4-0176 | Negative | 0.815 |
| Tc011095-13 | Positive | 1.293 | AT4-0013 | Negative | 0.100 |
| Tc011095-14 | Positive | 0.242 | AT4-0041 | Negative | 0.107 |
| Tc011095-15 | Positive | 0.636 | AT4-0062 | Negative | 0.28 |
| Tc011095-16 | Positive | 0.44 | AT4-0063 | Negative | 0.155 |
| Tc011095-17 | Positive | 3 | E4-0051 | Negative | 0.162 |
| Tc011095-18 | Positive | 1.651 | E4-0059 | Negative | 0.176 |
| Tc011095-19 | Positive | 0.19 | E4-0068 | Negative | 0.241 |
| Tc011095-20 | Positive | 0.916 | E4-0071 | Negative | 0.127 |
| Tc011095-21 | Positive | 0.715 | C4-0072 | Negative | 0.101 |
| Tc011095-22 | Positive | 1.336 | C4-0088 | Negative | 0.141 |
| Tc011095-23 | Positive | 1.037 | C4-0090 | Negative | 0.078 |
| Tc011095-24 | Positive | 0.332 | C4-0096 | Negative | 0.162 |
| Tc011095-25 | Positive | 0.413 | C4-0101 | Negative | 0.181 |
| Tc011095-26 | Positive | 0.266 | C4-0105 | Negative | 0.702 |
| Tc011095-27 | Positive | 1.808 | | | |
| Tc011095-28 | Positive | 0.238 | | | |
| Tc011095-29 | Positive | 0.266 | | | |
| Tc011095-30 | Positive | 1.563 | | | |
| Tc011095-31 | Positive | 0.352 | Sensitivity | 33/48 | 68.75% |
| Tc011095-32 | Positive | 0.208 | Specificity | 24/26 | 92.30% |
| Tc011095-33 | Positive | 0.656 | Mean Pos. | 0.9188 | |
| Tc011095-34 | Positive | 1.281 | Std Dev Pos. | 0.79 | |
| Tc011095-35 | Positive | 0.907 | Mean Neg. | 0.1508 | |
| Tc011095-36 | Positive | 0.429 | Std Dev Neg. | 0.06695 | |
| Tc011095-37 | Positive | 0.454 | | | |
| Tc011095-38 | Positive | 0.725 | | | |
| Tc011095-39 | Positive | 0.703 | | | |
| Tc0394-7 | Positive | 0.186 | | | |
| Tc0394-8 | Positive | 1.06 | | | |
| Tc0394-9 | Positive | 1.813 | | | |
| Tc0394-10 | Positive | 0.131 | | | |
| Tc0394-11 | Positive | 1.631 | | | |
| Tc0394-12 | Positive | 0.613 | | | |
| Tc0394-13 | Positive | 3 | | | |
| Tc0394-14 | Positive | 0.268 | | | |
| Tc0394-15 | Positive | 2.211 | | | |

Example 5

Serological Reactivity of Peptide Combinations

This example illustrates the diagnostic properties of several peptide combinations.

The TcLo1.2 peptide (contained within SEQ ID NO:35) was tested in combination with the synthetic peptide TcD and also the dual epitope peptides D/2 (which contains the TcD and the PEP-2 sequences) and D/E (which contains TcD and TcE sequences). These combinations were compared with the individual peptides as well as the tripeptide 2/DI/E, which contains TcD, TcE and PEP-2. The TcD sequence used was Ala Glu Pro Lys Ser Ala Glu Pro Lys Pro Ala Glu Pro Lys Ser (SEQ ID NO:53), the TcE sequence was Lys Ala Ala lie Ala Pro Ala Lys Ala Ala Ala Ala Pro Ala Lys Ala Ala Thr Ala Pro Ala (SEQ ID NO: 55), and the PEP2 sequence was Gly Asp Lys Pro Ser Pro Phe Gly Gln Ala Ala Ala Gly Asp Lys Pro Ser Pro Phe Gly Gln Ala (SEQ ID NO: 57).

Figure 6:
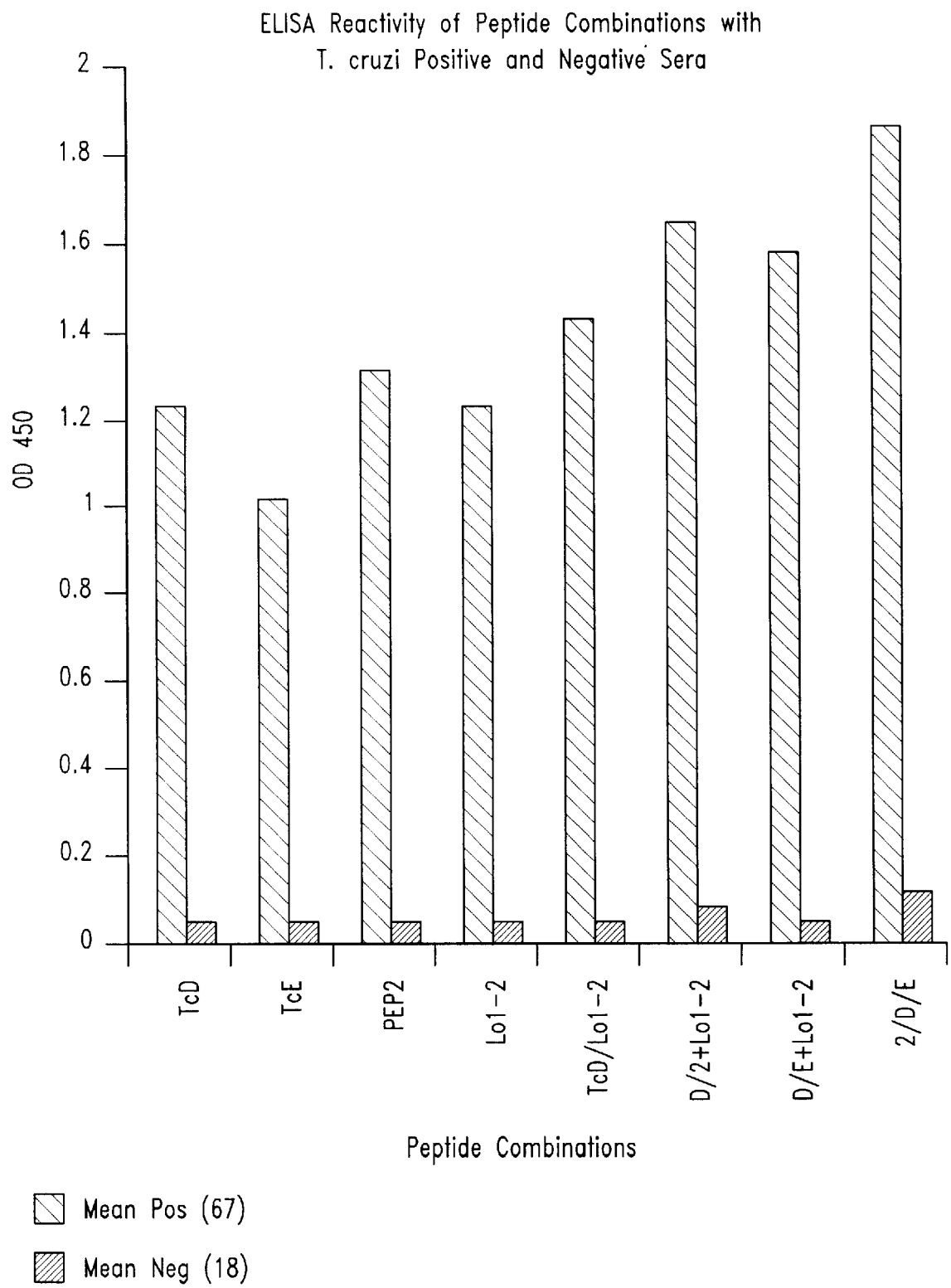
FIG. 6 is a graph depicting the ELISA reactivity of a series of polypeptide combinations with *T. cruzi* positive and negative sera.
Figure 7:
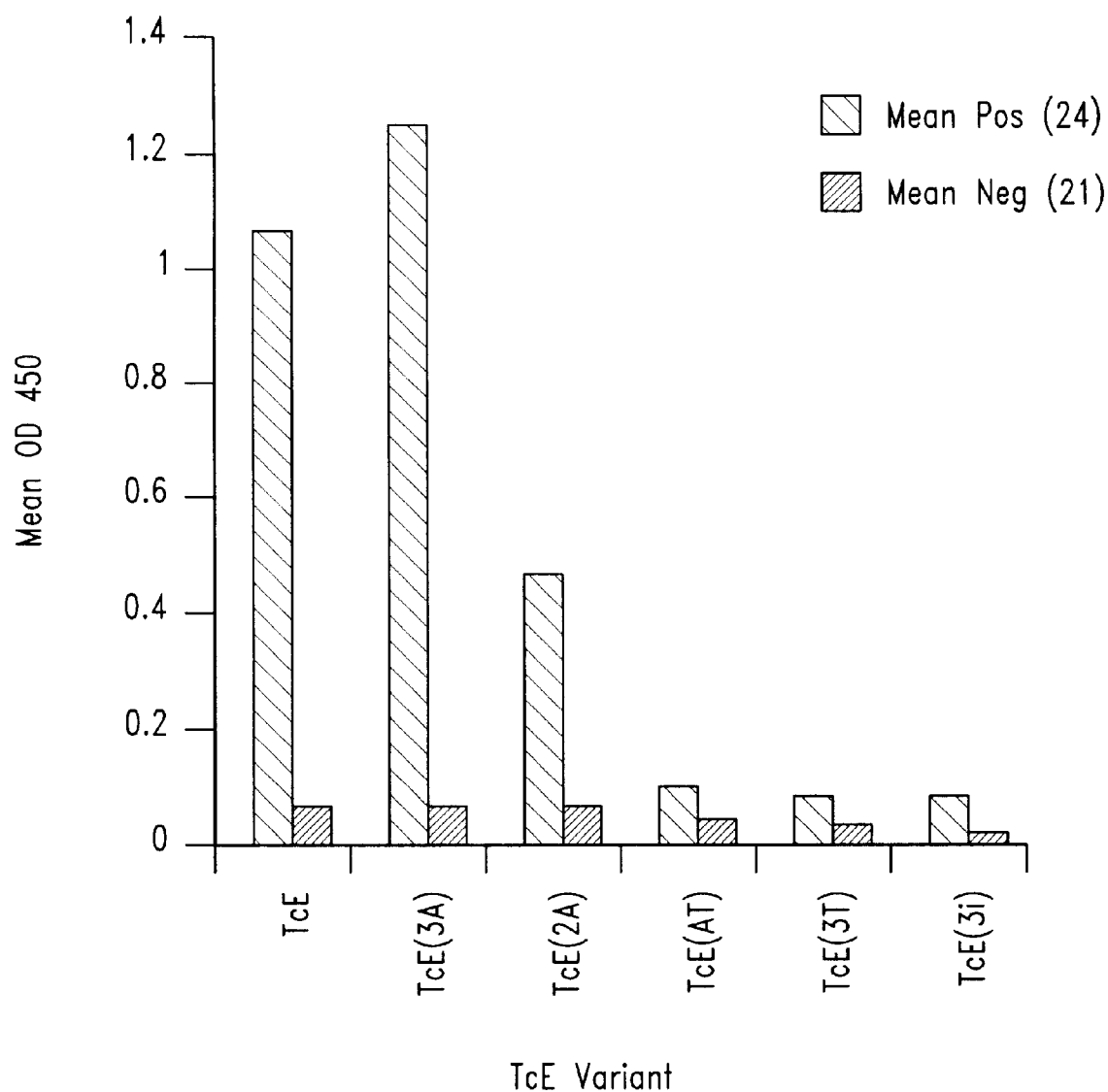
FIG. 7 is a graph presenting the ELISA reactivity of a series of TcE polypeptide variants with *T. cruzi* positive and negative sera.
Figure 8:
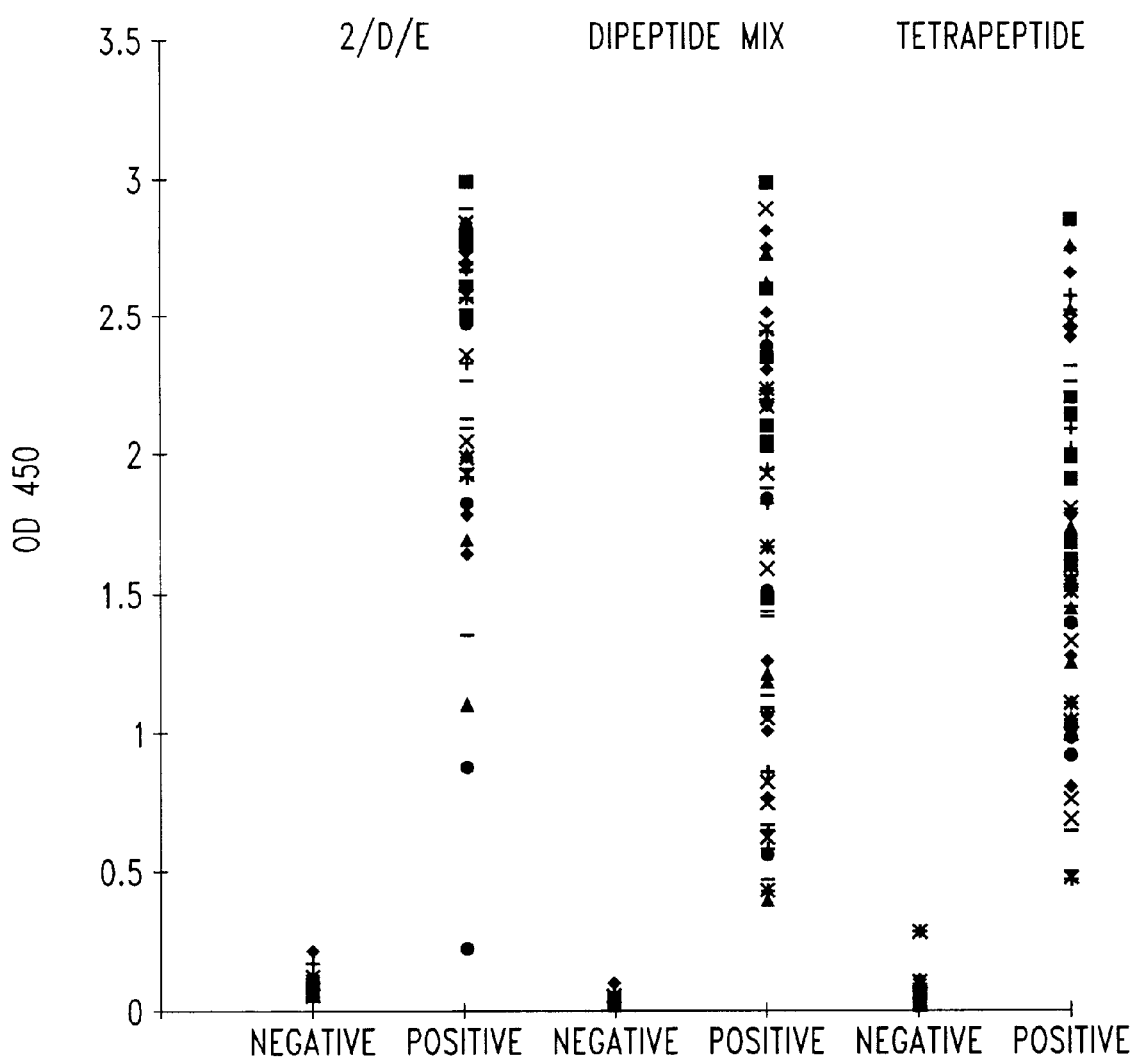
FIG. 8 is a graph comparing the ELISA reactivity of two dipeptides, a tripeptide and a tetrapeptide of the present invention with *T. cruzi* positive and negative sera.

The data are shown in FIG. 6. The results show that TcLo 1.2 can augment the reactivity of TcD, D/2 and D/E, as summarized in Table 2.

Table 2

Sensitivity of Peptide Combinations in the Detection of *T. cruzi* Infection

TABLE 2

Sensitivity of Peptide Combinations in the Detection of *T. cruzi* Infection

| Peptides | Number of Positives |
|---|---|
| TcD | 62/67 |
| TcE | 50/67 |
| PEP-2 | 66/67 |
| TcLo1.2 | 61/67 |
| TcD + TcLo1.2 | 66/67 |
| D/2 + TcLo1.2 | 67/67 |
| D/E + TcLo1.2 | 67/67 |
| 2/D/E | 67/67 |

These results demonstrate the use of *T. cruzi* antigens as described herein to enhance the serodiagnostic properties of other antigens.

Example 6

Serological Reactivity of TcE Repeat Sequences

This example illustrates the diagnostic properties of several TcE repeat sequences.

The repeat sequence region of the recombinant TcE contains several degeneracies, resulting in residues where an A (alanine), T (threonine) or I (isoleucine) can be present in the repeat sequence. In order to represent all degeneracies, the original sequence for the synthetic TcE peptide was made with an A, T and I in a single peptide containing three repeats (see Example 5). In order to further epitope map the repeat region and to determine the number of repeats required for serological activity, the following peptides were prepared as described in Example 2:

| | | |
|---|---|---|
| original TcE | KAAIAPAKAAAAPAKAATAPA | (SEQ ID NO:55) |
| TcE(3A) | KAAAAPAKAAAAPAKAAAAPA | (SEQ ID NO:58) |
| TcE(3T) | KAATAPAKAATAPAKAATAPA | (SEQ ID NO:59) |
| TcE(3I) | KAAIAPAKAAIAPAKAAIAPA | (SEQ ID NO:60) |
| TcE(2A) | KAAAAPAKAAAAPA | (SEQ ID NO:61) |
| TcE(AT) | KAAAAPAKAATAPA | (SEQ ID NO:62) |

The serological reactivity of these peptides was then compared. A total of 24 positive and 21 negative sera were tested with each of the TcE variants as the solid phase in an ELISA assay performed as described in Example 3, using 25 ng/well of peptide. The reactivity of the different peptides is shown in FIG. 7. The highest reactivity was seen with the 3-repeat peptide in which each repeat contained an A at the degenerate residue (TcE(3A)). This peptide displayed even higher reactivity than the original TcE sequence containing an A, T and I residue in the three repeats. The 3I and 3T variants by contrast were essentially negative with the *T. cruzi* positive samples tested. The sequence containing two repeats with A (TcE(2A)) was clearly less reactive than the 3A sequence and the two repeat sequence with an A and a T (TcE(AT)) was negative. Based on a cutoff of the mean of the negatives plus three standard deviations, the original TcE (A,T,I) detected 17 out of 24 positives and the 3A variant detected 19 out of 24 positives. It also appears that to obtain maximal serological activity at least three repeats are required.

Example 7

Serological Reactivity of Multi-epitope Peptide Combinations

This example illustrates the diagnostic properties of several multi-epitope peptide combinations.

Two dipeptides PEP-2/TcLo1.2, which contains the PEP-2 (SEQ ID NO:57) and TcLo1.2 (SEQ ID NO:35) sequences, and TcD/TcE, which contains the TcD (SEQ ID NO:53) and TcE (SEQ ID NO:55) sequences, were synthesized as described above in Example 2. The reactivity of these two dipeptides with *T. cruzi* antibody-positive sera was compared to that of the tripeptide 2/D/E. ELISA's were performed as described in Example 3 using PEP-21/TcLo1.2 at 250 ng/well and TcD/TcE at 50 ng/well. The results of this study are shown in FIG. 8. One *T. cruzi* positive serum found not to react with the tripeptide 2/D/E was used in screening for the TcLo1.2 epitope. This serum was detected by the TcLo1.2 epitope and also by the dipeptide mix (PEP-2/TcLo1.2 together with TcD/TcE) as expected.

A tetrapeptide containing the four immunoreactive *T. cruzi* epitopes PEP-2, TcD, TcE and TcLol.2 in a linear sequence, herein after referred to as 2/Lo/2E/D (SEQ ID NO:63) was synthesized as described in Example 2. This tetrapeptide was coated at 100 ng/well and its reactivity with *T. cruzi* positive and negative sera was assayed as described in Example 3. The reactivity of the tetrapeptide 2/Lo/2E/D is shown in FIG. 8. The one *T. cruzi* positive serum found not to react with the tripeptide 2/D/E was detected by the tetrapeptide as expected.

The four immunoreactive *T. cruzi* epitopes PEP-2, TcD, TcE and TcLo1.2 may also be linked into one reagent by the use of a 'branched' peptide originating from a lysine core residue. Orthogonal protection of the lysine, for example employing 9-Fluorenylmethoxycarbonyl (Fmoc) on the a-amino group and 1-(4,4-Dimethyl-2,6-dioxocyclohex-1-ylidene)ethyl (Dde) on the E-amino group, is used to permit selective deprotection of one amino group in the presence of the other, thereby allowing the synthesis of the first peptide chain from either the α- or ϵ- group on the lysine. This first peptide chain is terminated with a protecting group that is not removed during the course of the synthesis of the second peptide chain. For example, a tert-Butoxy carbonyl (Boc) amino acid could be used with the Dde and Fmoc combination. The remaining lysine amino protecting group is then removed before a second amino acid chain is synthesized from the second amino moiety. For example, ϵ-Dde is removed with 20% hydrazine. Cleavage of the branched peptide from a solid support and removal of the N-α-Boc moiety is carried out using trifluoroacetic acid, following standard protocols. Using this approach two independent amino acid sequences can be built from a 'core' lysine residue, as shown below, thus allowing various combinations of TcD, TcE, PEP2, TcLo1.2, and other epitopes to be coupled to the core residue. Purification of the resulting peptide is performed as described in Example 2.

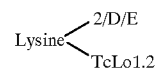

Example 8

Preparation of Multi-epitope Peptide Combinations using Recombinant DNA Technology This example illustrates the preparation of a fusion polypeptide (hereinafter referred to as TcF) of the peptides PEP-2 (SEQ ID NO: 57), TcD (SEQ ID NO: 53), TcE (SEQ ID NO: 55) and TcLo1.2 (SEQ ID NO: 35) using recombinant DNA technology.

The TcF polypeptide fusion was created by synthesizing overlapping phosphorylated oligonucleotides, annealing the matched oligonucleotide pairs to create double stranded DNA, ligating the annealed pairs with vector DNA that was cut with appropriate enzymes, and transforming into suitable bacteria host strains (XL2, Stratagene, La Jolla, Calif.) for sequencing. Once the correct sequence was obtained, the construct was subcloned into a modified pET28 vector and transformed into BLR pLYS S (Novagen, Madison, Wis.) for expression and purification.

For construction of the PEP2-TcD fusion, the matched pairs of oligonucleotides PDM-95 (SEQ ID NO: 66) and PDM-98 (SEQ ID NO: 67); PDM-96 (SEQ ID NO: 68) and PDM-99 (SEQ ID NO: 69); and PDM-97 (SEQ ID NO: 70) and PDM-100 (SEQ ID NO: 71) were synthesized, kinased and annealed. These three pairs of annealed oligos were then ligated, digested with EcoRI (New England Biolabs, Beverly, Mass.) and cloned into a modified T vector construct with Eco72I and EcoRI. For construction of the PEP2-TcD-TcE fusion, the following matched pairs of oligonucleotides were synthesized, kinased and annealed: PDM-103 (SEQ ID NO: 72) and PDM-105 (SEQ ID NO: 73); and PDM-104 (SEQ ID NO: 74) and PDM-106 (SEQ ID NO: 75). These two pairs of annealed oligos were ligated into the pT7ΔL2PEP2-TcD construct cut with Eco47III (New England Biolabs) and EcoRI.

For construction of the PEP2-TcD-TcE-Lo1.2 fusion, the two matched paris of oligonucleotides PDM-108 (SEQ ID NO: 76) and PDM-I 10 (SEQ ID NO: 77); and PDM-109 (SEQ ID NO: 78) and PDM- 110 (SEQ ID NO: 79) were synthesized, kinased and annealed. These two pairs of annealed oligonucleotides were ligated with the pT7ΔL2PEP2-TcD-TcE construct which had been cut with EagI, treated for blunt ends with T4 DNA polymerase and then cut with EcoRI. Due to an internal EagI site in the pT7ΔL2 vector, a PCR reaction was performed with the ligation mix as template in order to clone the full length PEP2-TcD-TcE-Lo1.2 construct. PCR was accomplished with the primers PDM-101 and PDM-107 (SEQ ID NOS: 80 and 81, respectively) using the following conditions:

96° C. 2 minutes

96° C. 15 seconds 61° C. 15 seconds, 72° C. 1 minute×40 cycles

72° C. 4 minutes.

Pful DNA polymerase (Stratagene, La Jolla, Calif.) was used for the PCR reaction. Following PCR, the DNA was subjected to an ethanol precipitation, digested with SmaI and EcoRI, and ligated into a modified T vector construct which had been digested with Eco72I and EcoRI.

The resulting clone was digested with Hind III (Gibco BRL, Gaitherburg, Md.) and Sph I (New England Biolabs), treated with T4 DNA polymerase for blunt ends and then religated in order to delete the vector's internal Eag I and Nsi I sites. This new clone was then digested with Eag I and Nsi I, treated with T4 DNA polymerase for blund ends, and religated in order to create a stop codon in frame at the end of the TcLo1.2 sequence. This clone was digested with NdeI and Eco RI, and subcloned into a modified pET28b vector cut with the same enzymes.

The resulting expression construct was transformed into BLR pLys S *E. coli* (Novagen) and grown overnight in LB broth with kanamycin (30 ug/ml, Sigma, St. Louis, Mo.) and chloramphenicol (34 ug/ml Sigma). The overnight culture (12 ml) was used to inoculate 500 ml of 2XYT with the same antibiotics and the culture was induced at an OD560 of 0.3–0.6 with IPTG to a final concentration of 1.0 mM. Four hours post-induction, the bacteria were harvested and sonicated in 20 mM Tris (8.0), 100 mM NaCl, 0.1% DOC, 20 ug/ml Leupeptin and 20 mM PMSF followed by centrifugation at 26,000×g. The fusion protein was found in the soluble supernatant after sonication. The supernantant was bound to a Pro-bond nickel resin column (Invitrogen, Carlsbad, Calif.). The column was washed with 50 ml of 20 mM Tris (8.0), 100 mM NaCl wash buffer and eluted with an increasing imidazole concentration. Specifically, the elutions were made with 50 mM, 100 mM and 500 mM imidazole in the 20 mM Tris (8.0), 100 mM NaCl wash buffer. The eluates containing the protein of interest were pooled and dialyzed against 10 mM Tris (8.0).

After dialysis, the protein was concentrated, sterile filtered and tested for endotoxins. Test results indicated a high level of endotoxin contamination. The sterile filtered protein was therefore purified over a High Q anion exchange column (Biorad, Hercules, Calif.), binding in 10 mM Tris (8.0) and eluting with a NaCl gradient up to 1 M in 10 mM Tris (8.0). The elutions containing the protein of interest were pooled and dialyzed against 10 mM Tris (8.0). After dialysis, the protein was reconcentrated, sterile filtered and a BCA assay (Pierce, Rockford, Ill.) was performed to determine protein concentration.

Figure 11:
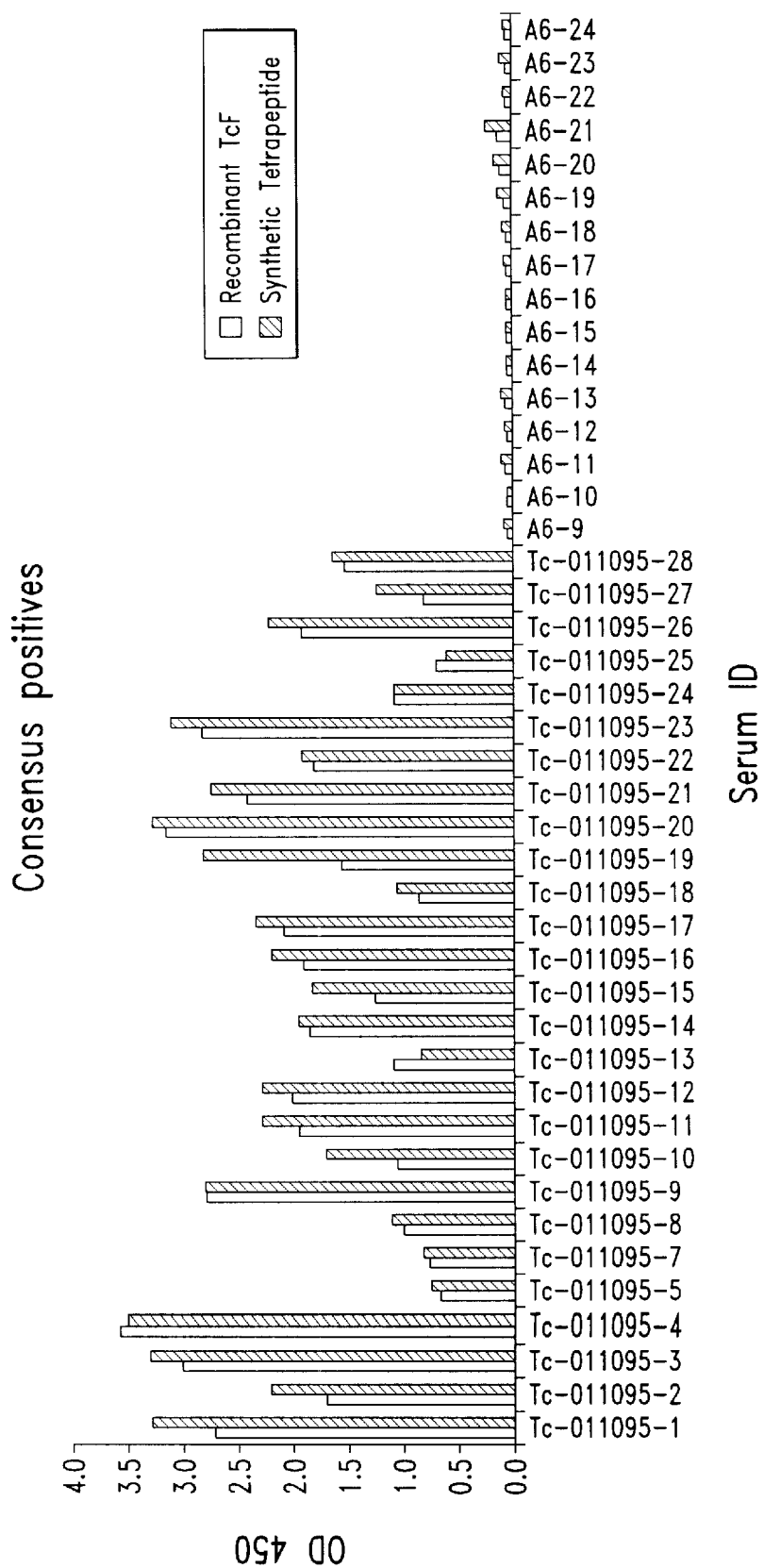
FIG. 11 is a graph comparing the ELISA reactivity of the recombinant fusion polypeptide TcF with sera from *T. cruzi* patients and from normal donors with the reactivity of the synthetic branched tetrapeptide 2/D/E/Lo1.2.

The reactivity of the recombinant fusion polypeptide TcF with sera from *T. cruzi* patients and from normal donors was examined by ELISA as described above. As shown in FIG. 11, the reactivity of TcF was found to be very similar to that of the branched synthetic tetrapeptide 2/D/E/Lo1.2.

It is envisioned that the order of the peptides in the recombinant fusion polypeptide TcF could be altered without significantly changing the activity of the polypeptide. Also, the inclusion of a Gly-Cys-Gly linkage between the peptides, as was employed in the synthetic tetrapeptide 2/Lo/2E/D, may enhance solid phase binding without significantly affecting the activity of the polypeptide.

Example 9

Comparison of the Serological Reactivity of TcHi29 and TcE

The antigen TcHi29 (SEQ ID NO:52) was shown to be a polymorph of the TcE repeat sequence. A TcHi29 peptide was synthesized that had the following sequence as compared to TcE.

| TcE | KAAIAPAKAAAAPAKAATAPA | (SEQ ID NO:55) |
|---|---|---|
| TcHi29 | KTAAPPAKTAAPPAKTAAPPA | (SEQ ID NO:64) |

Figure 9:
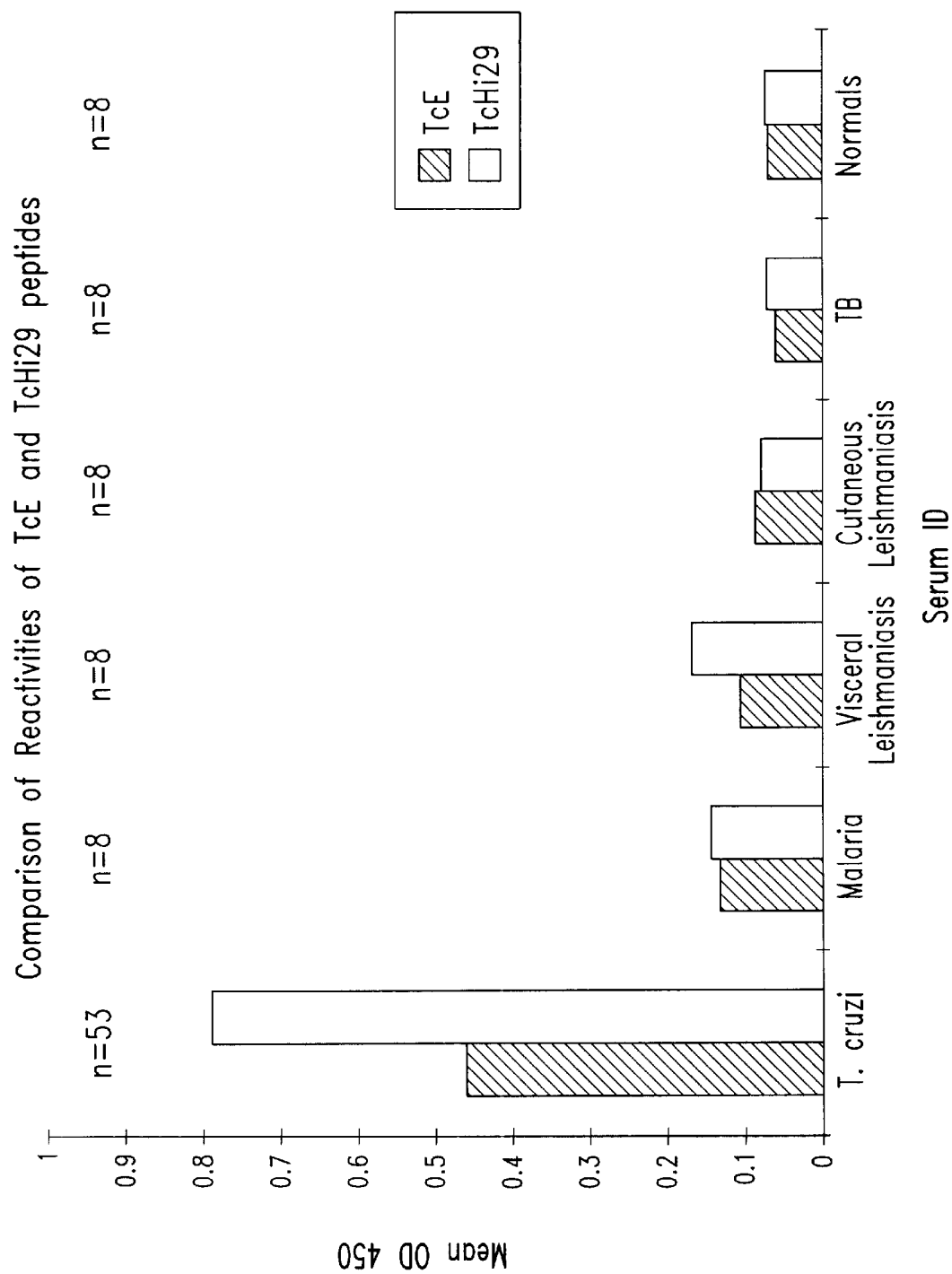
FIG. 9 is a graph presenting the ELISA reactivity of a representative polypeptide of the present invention (TcHi29) and of TcE with sera from normal individuals, *T. cruzi* patients, and patients with other diseases.
Figure 10:
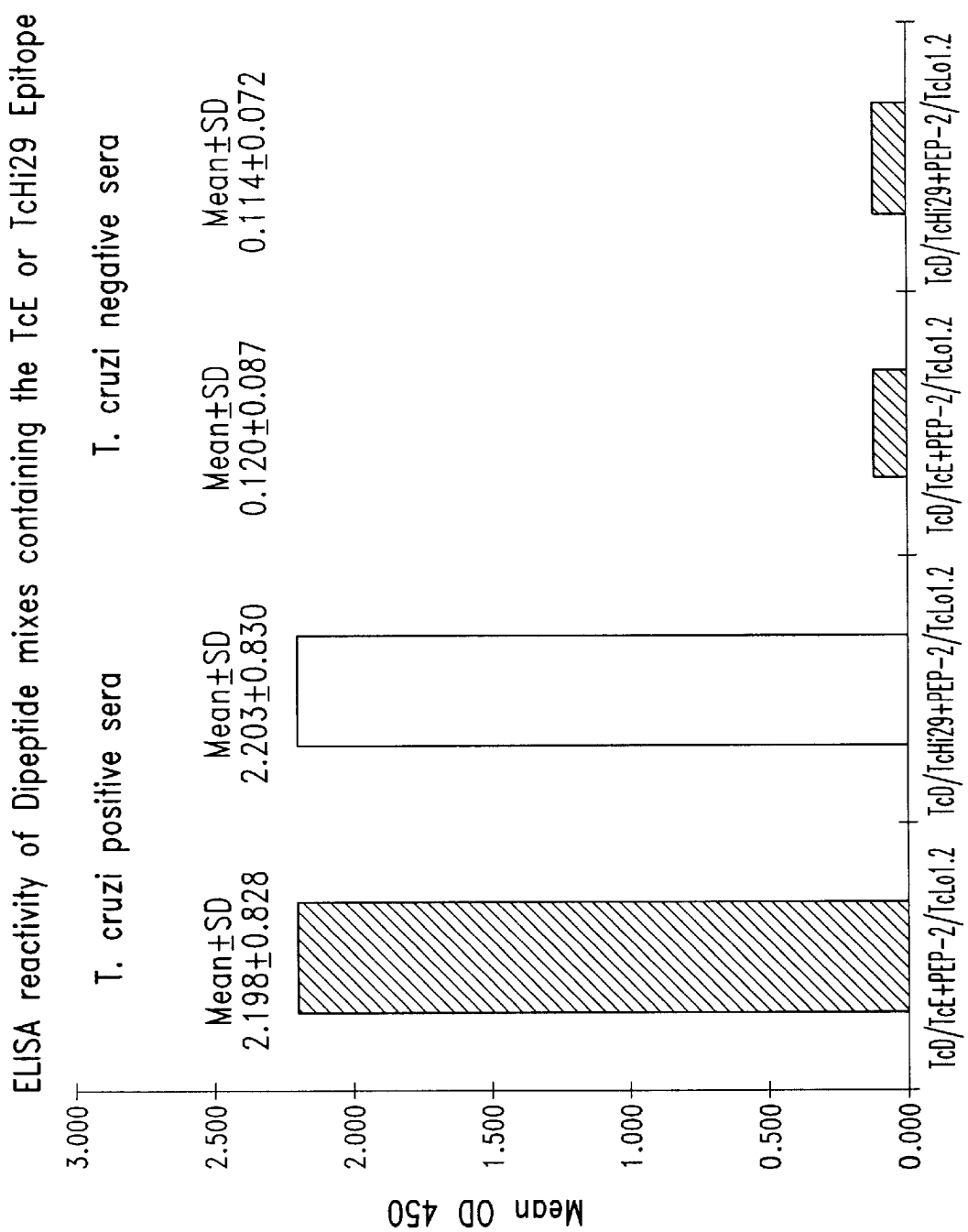
FIG. 10 is a graph comparing the ELISA reactivity of two representative dipeptide mixtures with *T. cruzi* positive and negative sera, one mixture including a TcE epitope and the other including a TcHi29 epitope of the present invention.

FIG. 9 shows a comparison of the reactivity of these two related seqences with sera from *T. cruzi* positive patients as well as from other disease categories, as determined by ELISA using the procedure described above. The data indicate little or no cross reactivity with the other disease groups tested but the distribution of reactivity amongst the *T. cruzi* positive sera partially overlapped for the two peptides. Of the 53 consensus positive samples tested, TcE detected 31/53 and TcHi 29 36/53. Within this group TcE and TcHi29 both detected 24 of the same sera. TcE detected 7 positive sera not detected by TcHi29, which in turn detected 12 positive sera missed by TcE. A dipeptide, TcD/FcHi29, was also synthesized and used in combination with the PEP-2/TcLo1.2 dipeptide in ELISA (100 ng/well TcD/TcHi29, 250 ng/well PEP-2/TcLo1.2) and compared with the TcD/TcE plus PEP-2/TcLo1.2 dipeptide combination. As shown in FIG. 10, the data indicates that the overall activity of the two mixes are similar for both the *T. cruzi* positive and negative populations studied and suggests that, in such peptide combinations, TcHi29 can be considered to be an alternative to TcE.

From the foregoing, it will be appreciated that, although specific embodiments of the invention have been described herein for the purpose of illustration, various modifications may be made without deviating from the spirit and scope of the invention.

What is claimed is:

1. A combination polypeptide comprising an amino acid sequence of SEQ ID NO: 35 and a heterologous peptide.

2. A combination polypeptide according to claim 1, wherein the polypeptide is prepared using recombinant DNA technology.

3. A combination polypeptide according to claim 1, wherein the polypeptide is prepared synthetically.

4. A method for detecting *T. cruzi* infection in a biological sample, comprising:
    (a) contacting the biological sample with a combination polypeptide according to any one of claims 1, 2 or 3; and
    (b) detecting in the biological sample the presence of antibodies that bind to the amino acid sequence of SEQ ID NO: 35, therefrom detecting *T. cruzi* infection in the biological sample.

5. A method for detecting *T. cruzi* infection in a biological sample, comprising:
    (a) contacting the biological sample with an isolated polypeptide comprising an amino acid sequence of SEQ ID NO: 35;
    (b) detecting in the biological sample the presence of antibodies that bind to the amino acid sequence of SEQ ID NO: 35 and therefrom detecting *T. cruzi* infection in the biological sample.

6. The method of claim 4, wherein the biological sample is selected from the group consisting of: blood, serum, plasma, saliva, cerebrospinal fluid and urine.

7. The method of claim 4, wherein the combination polypeptide is bound to a solid support.

8. The method of claim 7, wherein the solid support comprises a material selected from the group consisting of nitrocellulose, latex and plastic materials.

9. The combination polypeptide of claim 1 additionally comprising the sequences of SEQ ID NO: 53, 55 and 57.

10. An isolated combination polypeptide comprising at least two epitopes, each of the epitopes comprising an amino acid sequence of SEQ ID NO: 35.

11. The method of claim 5 wherein the biological sample is selected from the group consisting of: blood, serum, plasma, cerebrospinal fluid and urine.

12. The method of claim 5 wherein the isolated polypeptide is bound to a solid support.

13. The method of claim 12 wherein the solid support comprises a material selected from the group consisting of nitrocellulose, latex and plastic materials.

\* \* \* \* \*